US012617828B2

(12) United States Patent (10) Patent No.: US 12,617,828 B2
Li et al. (45) Date of Patent: May 5, 2026

(54) GENETICALLY MODIFIED IMMUNE CELL, PREPARATION METHOD THEREFOR, AND APPLICATION

(71) Applicant: SHENZHEN IN VIVO BIOMEDICINE TECHNOLOGY LIMITED COMPANY, Guangdong (CN)

(72) Inventors: Peng Li, Guangdong (CN); Zhiwu Jiang, Guangdong (CN); Zhaoyang Tang, Guangdong (CN); Rui Liao, Guangdong (CN); Xiaohan Huang, Guangdong (CN); Simiao Lin, Guangdong (CN); Suna Wang, Guangdong (CN); Youguo Long, Guangdong (CN); Qiting Wu, Guangdong (CN); Yao Yao, Guangdong (CN)

(73) Assignee: SHENZHEN IN VIVO BIOMEDICINE TECHNOLOGY LIMITED COMPANY, Guangdong (CN)

( * ) Notice: Subject to any disclaimer, the term of this patent is extended or adjusted under 35 U.S.C. 154(b) by 1164 days.

(21) Appl. No.: 17/600,884

(22) PCT Filed: May 6, 2020

(86) PCT No.: PCT/CN2020/088806
§ 371 (c)(1),
(2) Date: Oct. 1, 2021

(87) PCT Pub. No.: WO2020/200325
PCT Pub. Date: Oct. 8, 2020

(65) Prior Publication Data
US 2022/0185858 A1 Jun. 16, 2022

(30) Foreign Application Priority Data

Apr. 3, 2019 (CN) .......................... 201910267702.9
May 6, 2019 (CN) .......................... 201910372692.5

(51) Int. Cl.
| | |
|---|---|
| C07K 14/54 | (2006.01) |
| A61K 40/11 | (2025.01) |
| A61K 40/31 | (2025.01) |
| A61K 40/35 | (2025.01) |
| A61K 40/42 | (2025.01) |
| A61P 35/00 | (2006.01) |
| C07K 14/705 | (2006.01) |
| C07K 16/28 | (2006.01) |
| C07K 16/30 | (2006.01) |
| C07K 16/32 | (2006.01) |
| C12N 5/0783 | (2010.01) |

(52) U.S. Cl.
CPC .......... *C07K 14/5412* (2013.01); *A61K 40/11* (2025.01); *A61K 40/31* (2025.01); *A61K 40/35* (2025.01); *A61K 40/4211* (2025.01); *A61K*
*40/4257* (2025.01); *A61K 40/4261* (2025.01); *A61P 35/00* (2018.01); *C07K 14/70503* (2013.01); *C07K 16/2803* (2013.01); *C07K 16/303* (2013.01); *C07K 16/3069* (2013.01); *C07K 16/3092* (2013.01); *C07K 16/32* (2013.01); *C12N 5/0636* (2013.01); *A61K 2239/38* (2023.05); *A61K 2239/48* (2023.05); *A61K 2239/53* (2023.05); *A61K 2239/55* (2023.05); *C07K 2317/622* (2013.01); *C07K 2319/33* (2013.01)

(58) Field of Classification Search
CPC .................................................. C07K 14/5412
See application file for complete search history.

(56) References Cited

U.S. PATENT DOCUMENTS

| | | | |
|---|---|---|---|
| 5,536,657 A | 7/1996 | Chua et al. | |
| 7,112,436 B1 | 9/2006 | Rose-John | |
| 8,394,367 B2 * | 3/2013 | Revel ...................... | A61P 25/02 514/44 R |
| 10,093,717 B2 * | 10/2018 | Li ........................... | A61P 35/00 |
| 2005/0238622 A1 * | 10/2005 | Axelrod ............. | A61K 38/1793 514/44 R |

(Continued)

FOREIGN PATENT DOCUMENTS

| | | |
|---|---|---|
| CN | 102089326 A | 6/2011 |
| CN | 102264390 A | 11/2011 |

(Continued)

OTHER PUBLICATIONS

Snyers et al. Enhancement of IL-6 Teceptor B Chain (gp 130( Expression by IL-6, IL-1 and TNF in Human Epithelial Cells. Biochemical and Biophysical Research Communications 185: 902-908 (Year: 1992).*

(Continued)

*Primary Examiner* — James D Schultz
*Assistant Examiner* — Keenan A Bates
(74) *Attorney, Agent, or Firm* — ArentFox Schiff LLP; Daniel W. Clarke

(57) ABSTRACT

Provided are a genetically modified immune cell, a preparation method therefor, and an application. The immune cell overexpresses HIL-6 and/or L-GP130. HIL-6 or L-GP130 continuous overexpression/conditionally induced overexpression in the immune cell reduces the side effects of CAR-T therapy while maintaining immune and anti-tumour effects, and has potential value in the treatment of malignant tumours and AIDS.

11 Claims, 9 Drawing Sheets

Specification includes a Sequence Listing.

(56)                References Cited

U.S. PATENT DOCUMENTS

| | | | | |
|---|---|---|---|---|
| 2011/0217274 A1* | 9/2011 | Reld | A61P 1/00 | |
| | | | 435/325 | |
| 2018/0022801 A1 | 1/2018 | Garcia-Martinez et al. | | |
| 2018/0057794 A1* | 3/2018 | Rubinstein | A61K 38/2013 | |
| 2018/0214527 A1* | 8/2018 | Wang | A61K 40/11 | |

FOREIGN PATENT DOCUMENTS

| | | | |
|---|---|---|---|
| CN | 107573419 A | 1/2018 | |
| CN | 109468284 A | 3/2019 | |
| CN | 110055224 A | 7/2019 | |
| EP | 2992898 A1 | 3/2016 | |
| IN | 107827990 A | 3/2018 | |
| WO | 2010081738 A1 | 7/2010 | |
| WO | 2011/063198 A2 | 5/2011 | |
| WO | 2011/063198 A3 | 5/2011 | |
| WO | 2018073391 A1 | 4/2018 | |
| WO | 2018103502 A1 | 6/2018 | |
| WO | 2019076489 A1 | 4/2019 | |
| WO | WO-2019162521 A1 * | 8/2019 | A61K 31/713 |

OTHER PUBLICATIONS

UniProt (GP130—*Homo sapiens* (Human) https://www.uniprot.org/uniprotkb/P40189/entry#function (Year: 2025).*

Dechow et al. GP130 activation induces myeloma and collaborates with MYC. J Clin Invest. 124:5263-5274. (Year: 2014).*

Stuhlmann-Laeisz Forced Dimerization of gp130 Leads to Constitutive STAT3 Activation, Cytokine-independent Growth, and Blockade of Differentiation of Embryonic Stem Cells. Molecular Biology of the Cell 17. 2986-2995. (Year: 2006).*

GenBank (Human membrane glycoprotein gp130 mRNA, complete cds; M57230.1) https://www.ncbi.nlm.nih.gov/nuccore/M57230 (Year: 1995).*

GenBank (Synthetic human rJunLZ leucine zipper domain (junLZ) gene, complete cds; U08409.1) https://www.ncbi.nlm.nih.gov/nucleotide/U08409.1?report=genbank&log$=nuclalign&blast_rank=1&RID=W43BK4BU016 (Year: 1997).*

Sasaki et al. LacdiNAc (GalNAcb1-4GIcNAc) Contributes to Self-Renewal of Mouse Embryonic Stem Cells by Regulating Leukemia Inhibitory Factor/STAT3 Signaling. Stem Cells 29:641-650. (Year: 2011).*

Vosjan et al. Nanobodies Targeting the Hepatocyte Growth Factor: Potential New Drugs for Molecular Cancer Therapy. Mol Cancer Ther 11: 1017-1025. (Year: 2012).*

Vosjan et al. Supplemental Nanobodies Targeting the Hepatocyte Growth Factor: Potential New Drugs for Molecular Cancer Therapy. Mol Cancer Ther 11: 1017-1025. (Year: 2012).*

Dechow et al. Supplemental GP130 activation induces myeloma and collaborates with Myc. J Clin Invest. 124:5263-5274. (Year: 2014).*

Palumbo et al. Melphalan, Prednisone, and Lenalidomide for Newly Diagnosed Myeloma: Kinetics of Neutropenia and Thrombocytopenia and Time-to-Event Results. Clinical Lymphoma & Myeloma 9: 145-150. (Year: 2009).*

Sturm et al. Functional hyper-IL-6 from vaccinia virus-colonized tumors triggers platelet formation and helps to alleviate toxicity of mitomycin C enhanced virus therapy. Journal of Translational Medicine 10: 1-15. (Year: 2012).*

Calton et al. Oncolytic Viruses for Multiple Myeloma Therapy. Cancers 10: 1-16. (Year: 2018).*

Garfall et al. Anti-CD19 Car T cells with high-dose melphalan and autologous stem cell transplantation for refractory multiple myeloma. JCI Insight 3: 1-14. (Year: 2018).*

International Search Report dated Aug. 12, 2020, International Application No. PCT/CN2020/088806 (8 pgs.).

Peters, et al., "The Function of the Soluble Interleukin 6 (IL-6) Receptor In Vivo: Sensitization of Human Soluble IL-6 Receptor Transgenic Mice Toward IL-6 and Prolongation of the Plasma Half-life of IL-6," Journal of Experimental Medicine, vol. 183, No. 4, Apr. 1996, ISSN: 022-1007, pp. 1399-1406.

Takeda, et al., "WSX-1 Over-expression in CD4 (+) T Cells Leads to Hyperproliferation and Cytokine Hyperproduction in Response to TCR Stimulation," International Immunology, vol. 17, No. 7, Jul. 2005, ISSN: 9953-8178, pp. 889-897.

NCBI GenPept Protein Sequence Record, "interleukin-6 receptor subunit beta isoform 8 [*Homo sapiens*]" NCBI Reference Sequence: NP_001351208.1, pp. 1-5.

Qie et al., "Induction of anti-hepatocellular carcinoma immunity by Hyper-IL-6 gene in vivo," Chin J Cell Mol Immunol, vol. 28, No. 9, 2012, pp. 899-902.

Qin et al., "Construction of DNA vaccine with HIV-1 gag and hIL-2/hIL-6 and its immunological study," Immunological Journal, vol. 17, No. 1, Jan. 2001, pp. 5-8.

Rose-John et al., "IL-6 Trans-Signaling via the Soluble IL-6 Receptor: Importance for the Pro-Inflammatory Activities of IL-6," International Journal of Biological Sciences, vol. 8, No. 9, 2012, pp. 1237-1247.

Yang et al., "Advances in Structural Base of Interaction Between hIL-6 and Its Receptor and Antagonist of hIL-6," Chinese Journal of Biochemistry and Molecular Biology, vol. 20, No. 6, 2004, pp. 707-712.

First Office Action of Chinese Patent Application No. 201910372692.5 mailed on Sep. 27, 2021, along with English language translation thereof.

Kallen, K.-J., "The role of transsignalling via the agonistic soluble IL-6 receptor in human diseases," 2002, Biochimica et Biophysica Acta (BBA)—Molecular Cell Research, vol. 1592, No. 3, pp. 323-343, 21 pages.

Jiang et al., "IL-6 trans-signaling promotes the expansion and anti-tumor activity of Car T cells," Leukemia 35, pp. 1380-1391, DOI: 10.1038/s41375-020-01085-1 (2021), 12 pages.

Stuhlmann-Laeisz et al., "Forced dimerization of gp130 leads to constitutive STAT3 activation, cytokine- Independent growth, and blockade of differentiation of embryonic stem cells," Molecular Biology of the Cell, vol. 17, No. 7, pp. 2986-2995, DOI: 10.1091/mbc.e05-12-1129 (2006), 10 pages.

Examination Report No. 1 in Australian Application No. 2020255735 dated May 17, 2023, 14 pages.

* cited by examiner

Chimeric antigen receptor

■ Signal peptide (IgM and other signal peptides)

▦ scFv segments that recognize antigens (CD19, GPC3, MUC1, etc.)

☐ Transmembrane region (CD28 and other transmembrane regions)

▦ Intracellular co-stimulatory domain
(combination of intracellular co-stimulatory domains of one
or more activation signal molecules such as TLR3,
CD28/4-1BB, DAP10, etc.)

▨ CD3ζ

HIL-6

GENETICALLY MODIFIED IMMUNE CELL, PREPARATION METHOD THEREFOR, AND APPLICATION

CROSS-REFERENCE TO RELATED APPLICATIONS

This application is a national stage application, filed under 35 U.S.C. § 371, of International Application No. PCT/CN2020/088806, filed May 6, 2020, which claims the benefit of priority under 35 U.S.C. § 119 (e) to CN Application No: 201910267702.9, filed Apr. 3, 2019 and CN application No. 201910372692.5, filed May 6, 2019, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Sep. 6, 2021 is named 51766-502N01US ST25_Sequence.txt and is 88 KB in size.

TECHNICAL FIELD

The present application belongs to the field of biotechnology, relates to a genetically modified immune cell, a preparation method therefor, and use thereof, and in particular, relates to an immune cell overexpressing HIL-6 and/or L-GP130, a preparation method therefor, and use thereof.

BACKGROUND

The clinical application of anti-CD19 chimeric antigen receptor (CAR) T cells (tisagenlecleucel and axicabtagene ciloleucel) has shown that such cells have a significant killing effect on CD19 positive B-cell malignant tumors. However, there are still many problems in CAR T cell therapy. In the treatment of leukemia, the CAR T cell therapy has the problem of a high recurrence rate, and the promotion of the maintenance of CAR T cells and the formation of memory T cells may be the technical breakthrough to solve this problem. In addition, the results of clinical treatment of anti-CD19 CAR T cells show that there is a positive correlation between the response rate of patients to the CAR T cell therapy and the occurrence of cytokine release syndrome (CRS), and CRS may lead to side effects such as CAR-T cell-related encephalopathy syndrome (CRES), which seriously limits the clinical application of CAR T cells. In the treatment of solid tumors, CAR T cells have a poor curative effect, and no related clinical research breakthrough has been reported yet.

The activation and expansion of T cells are required for effective coordination signals, including T-cell receptor (TCR) signals (first signal), co-stimulatory signals (second signal), and cytokine signals (third signal). Molecules carrying the third signal (such as IL-12, IL-7, and IL-15) significantly improve the expansion, migration, persistence, and anti-tumor efficacy of CAR T cells.

CRS is detected with interleukin 6 (IL-6) as the indicator. As a pleiotropic cytokine in the family of chemokines, IL-6 is mainly generated in mononuclear macrophages, Th2 cells, vascular endothelial cells, and fibroblasts. IL-6 has many target cells and complex biological effects. IL-6 can trigger a wide range of cellular and physiological reactions, including immune response, inflammation, hematopoiesis, and tumorigenesis, by regulating growth, gene activation, proliferation, survival, and differentiation of cells. IL-6 forms a protein complex by binding to non-signal transducer IL-6Rα, then dimerizes with subunit glycoprotein 130 (GP130), and initiates signal transduction cascades through transcription factors, Janus kinases (JAKs), signal transducers, and transcription activators (STATs). The binding of IL-6 and IL-6R includes membrane-binding IL-6R (mIL-6R) and soluble IL-6R (sIL-6R), which are called classical signal transduction and nonclassical signal transduction, respectively.

In the existing art, the effect of IL-6 is usually inhibited by using IL-6 monoclonal antibody (PMID: 27049586) or IL-1 beta monoclonal antibody (PMID: 29808007 and PMID: 29808005), or the side effects of CAR T cell therapy are inhibited by targeting IL-6 and IL-6R (EP3305890A1, US20180369282A1, U.S. Ser. Nos. 15/018,797, and 15/106, 657). However, the mechanism of action of IL-6 is complex and has two sides. One-sided inhibition of IL-6 may affect the anti-tumor effect of CAR T cells.

WO2017007985 discloses a method for treating cancer using IL-6. However, the treatment with IL-6 alone may activate both membrane-binding IL-6R (mIL-6R) and soluble IL-6R (sIL-6R). mIL-6R is mostly related to the non-tumor killing. Excessive activation of mIL-6R may interfere with the function of immune cells and consume the amount of IL-6 in soluble IL-6R.

Early reports have shown that IL-6 has anti-tumor effects in mouse models, but mouse models have limited the discovery of side effects of IL-6. With the development of science and technology, researchers have gradually realized that IL-6 can not only cause serious side effects, but also cause inflammatory microenvironment, trigger cytokine storm in patients, and promote tumor growth or immune escape when IL-6 is used systemically. In recent study, the side effects of IL-6 are often blocked by using IL-6 receptor monoclonal antibody and knocking out IL-6 receptor (PMID: 27076371). However, blocking IL-6 will affect the maximization of the anti-tumor effect of immune cells and the effect of anti-tumor treatment.

SUMMARY

The present application provides a genetically modified immune cell, a preparation method therefor, and use thereof. The ability of amplification, migration, and tumor killing of the immune cell is significantly enhanced, the infiltration in solid tumors is improved, and the immune cell has potential value in the treatment of solid tumors.

In the first aspect, the present application provides an immune cell, which overexpresses HIL-6 and/or L-GP130.

In the present application, complex IL-6 (hyper-IL-6, known as HIL-6) is a protein complex of IL-6 and IL-6 receptor alpha; and glycoprotein 130 (GP130), also known as CD130, IL6ST or IL6 beta, can bind to IL-6 receptor, IL-11 receptor, IL-12 receptor, IL-27 receptor, leukemia inhibitory factor receptor (LIF), oncogen M receptor (OSM), ciliary neurotrophic factor (CNTF), cardiotrophin-1 (CT-1), cardiotrophin-like cytokine (CLC), and Kaposi's sarcoma-associated herpesvirus interleukin-6 (KSHV-IL6).

In the present application, immune cells treated with/overexpressing/inducibly overexpressing HIL-6 or L-GP130 reduce the side effects of CAR T during treatment while maintaining the anti-tumor effect.

Preferably, the HIL-6 has an amino acid sequence as shown in SEQ ID NO: 1 or having 80% or more homology with and the same or similar activity as SEQ ID NO: 1.

Preferably, the HIL-6 has a nucleic acid sequence as shown in SEQ ID NO: 2.

Preferably, the L-GP130 has an amino acid sequence as shown in SEQ ID NO: 3 or having 80% or more homology with and the same or similar activity as SEQ ID NO: 3.

Preferably, the L-GP130 has a nucleic acid sequence as shown in SEQ ID NO: 4.

Preferably, the immune cell includes any one or a combination of at least two of a T cell, a B cell, an NK cell or macrophage.

Preferably, the T cell includes any one or a combination of at least two of a CD4+ T cell, a CD8+ T cell, a CD4+CD8+ T cell, an NKT cell or a gamma delta (γδ) T cell, preferably a CD4+ T cell, a CD8+ T cell or a CD4+CD8+ T cell, and further preferably a Th1 cell, a memory T cell or a central memory T cell.

Preferably, the immune cell is modified with one or two of CAR molecules and/or TCR molecules.

Preferably, an antigen recognized by an extracellular scFv sequence of the CAR molecule includes any one of 5T4, alpha-5 beta-1 (α5β1)-integrin, 707-AP, AFP, ART-4, B7H4, B7-H3, BAGE, beta (β)-integrin/m, Bcr-abl, MN/C IX antibody, CA125, CAMEL, CAP-1, CASP-8, CD4, CD19, CD20, CD22, CD25, CDC27/m, CD30, CD33, CD52, CD56, CD80, CDK4/m, CEA, CT, Cyp-B, DAM, EGFR, ErbB3, ELF2M, EMMPRIN, EpCam, ETV6-AML1, G250, GAGE, GnT-V, Gp100, HAGE, HER-2, HLA-A*0201-R170I, HPV-E7, HSP70-2M, HST-2, hTERT, hTRT, iCE, IGF-1R, IL-2R, IL-5, KIAA0205, LAGE, LDLR/FUT, MAGE, MART-1/melan-A, MART-2/Ski, MC1R, Mesothelin, myosin/m, MUC1, MUM-1, MUM-2, MUM-3, PSCA, NA88-A, PAP, protease-3, GPC3, p190minor bcr-abl, Pml/RARR, PRAME, PSA, PSM, PSMA, RAGE, RU1, RU2, SAGE, SART-1, SART-3, survivin, TEL/AML1, PD-1, PD-L1, CTLA-4, TIM3, LAG3, TGF3, TPI/m, TRP-1, TRP-2, TRP-2/INT2, VEGF, WT1, IL-13RIN, CD123, GUCY2C, NY-Eso-1 or NY-Eso-B, preferably any one of CD19, MUC1, GPC3, Mesothelin, PSCA or HER2.

Preferably, scFv 1 of the anti-CD19 CAR has an amino acid sequence as shown in SEQ ID NO: 5 and a nucleic acid sequence as shown in SEQ ID NO: 6.

Preferably, scFvs 2 to 7 of the anti-CD19 CAR have amino acid sequences as shown in SEQ ID NOs: 7 to 12.

Preferably, an scFv of the anti-GPC3 CAR has an amino acid sequence as shown in SEQ ID NO: 13 and a nucleic acid sequence as shown in SEQ ID NO: 14.

Preferably, an scFv of the anti-MUC1 CAR has an amino acid sequence as shown in SEQ ID NO: 15 and a nucleic acid sequence as shown in SEQ ID NO: 16.

Preferably, an scFv of the anti-Mesothelin has an amino acid sequence as shown in SEQ ID NO: 17 and a nucleic acid sequence as shown in SEQ ID NO: 18.

Preferably, an scFv of the anti-PSCA has an amino acid sequence as shown in SEQ ID NO: 19 and a nucleic acid sequence as shown in SEQ ID NO: 20.

Preferably, an scFv of the anti-HER2 has an amino acid sequence as shown in SEQ ID NO: 21 and a nucleic acid sequence as shown in SEQ ID NO: 22.

Preferably, the CAR molecule has an intracellular co-stimulatory signal transduction domain including an intracellular domain of any one of molecules of CD28, 4-1BB, TLR1, TLR2, TLR3, TLR4, TLR5, TLR6, TLR7, TLR8, TLR9, TLR10, DAP10, CD27, OX40, CD30, CD40, ICOS, lymphocyte function-associated antigen 1, CD2, CD7, LIGHT, NKG2C, NKG2D, NKp46, NKp30, NKp44, DNAM1, B7-H3, and CD83, or including a combination of intracellular domains of at least two of these molecules.

Preferably, the TLR2 has an amino acid sequence as shown in SEQ ID NO: 23 and a nucleic acid sequence as shown in SEQ ID NO: 2.

Preferably, the 4-1BB has an amino acid sequence as shown in SEQ ID NO: 25 and a nucleic acid sequence as shown in SEQ ID NO: 26.

Preferably, the CD28 has an amino acid sequence as shown in SEQ ID NO: 27 and a nucleic acid sequence as shown in SEQ ID NO: 28.

Preferably, the TLR1 has an amino acid sequence as shown in SEQ ID NO: 29 and a nucleic acid sequence as shown in SEQ ID NO: 30.

Preferably, the DAP10 has an amino acid sequence as shown in SEQ ID NO: 31 and a nucleic acid sequence as shown in SEQ ID NO: 32.

Preferably, a signal peptide of the CAR molecule has a nucleic acid sequence as shown in SEQ ID NO: 33.

Preferably, a transmembrane region of the CAR molecule has a nucleic acid sequence as shown in SEQ ID NO: 34.

Preferably, CD3 of the CAR molecule has a nucleic acid sequence as shown in SEQ ID NO: 35.

In the second aspect, the present application provides a method for preparing the immune cell described in the first aspect, which includes overexpressing HIL-6 and/or L-GP130 in an immune cell.

Preferably, the overexpression includes constitutive overexpression and/or conditionally-induced overexpression, preferably conditionally-induced overexpression.

According to the present application, the secretion of HIL-6 out of immune cells may cause intense local immune effects, lead to inflammation and fever of the body, raise the risk of cytokine storm caused by tumor immunotherapy, and have certain safety risks. In the present application, the conditionally-induced expression of HIL-6 is preferably adopted.

L-GP130 is included for perfection in terms of the safety risk of the external secretion of HIL-6. L-GP130 does not secreted out externally, has no stimulation effect on other immune cells, does not cause systemic or local immune effects, does not cause cytokine storm, and does not increase the risk of the cytokine storm. Moreover, it maintains the promotion effect of HIL-6 on the anti-tumor effect of specifically expressed immune cells or modified immune cells, and can promote the anti-tumor effect of T cells and CAR T cells. However, considering that the overexpression of L-GP130 in liver cells and other tissues may have certain tumorigenesis risk, L-GP130 is preferably induced conditionally to be expressed.

Preferably, the conditionally-induced overexpression includes CAR recognition activation-induced overexpression and/or exogenous compound-induced overexpression.

Preferably, in a system of the CAR recognition activation-induced overexpression, a plasmid vector includes any one or a combination of at least two of pUC57-CAR, pUC57-NFAT sequence-IL2 promoter-HIL-6 or pUC57-NFAT sequence-IL2 promoter-L-GP130.

Preferably, the NFAT has a nucleic acid sequence as shown in SEQ ID NO: 37.

Preferably, the IL2 promoter has a nucleic acid sequence as shown in SEQ ID NO: 38.

Preferably, the exogenous compound includes doxycycline.

Preferably, the overexpression is performed in a manner of liposome transduction, electrical transduction or viral transduction.

Preferably, a vector used for the overexpression includes a viral vector and/or a PB vector.

Preferably, the viral vector includes any one or a combination of at least two of a lentiviral vector, an adenoviral vector or a retroviral vector, preferably a lentiviral vector, and further preferably a lentiviral vector pWPXLd.

Preferably, the PB vector has a nucleic acid sequence as shown in SEQ ID NO: 36.

Preferably, the lentiviral vector pWPXLd has a nucleic acid sequence as shown in SEQ ID NO: 44.

In the third aspect, the present application provides a pharmaceutical composition, which includes the immune cell described in the first aspect.

Preferably, the pharmaceutical composition further includes any one or a combination of at least two of a pharmaceutically acceptable carrier, an excipient or a diluent.

In the fourth aspect, the present application includes use of the immune cell described in the first aspect and/or the pharmaceutical composition described in the third aspect for preparing a drug for the treatment tumors and/or AIDS caused by HIV virus infection.

Preferably, the tumor includes a hematological tumor and/or a solid tumor.

Preferably, the hematological tumor includes leukemia, multiple myeloma or malignant lymphoma.

Preferably, the leukemia includes B-cell acute lymphoblastic leukemia, T-cell acute lymphoblastic leukemia, acute myeloid leukemia, chronic lymphocytic leukemia or chronic myeloid leukemia.

Preferably, the solid tumor includes lung cancer, liver cancer, breast cancer, nephroblastoma, glioma, neuroblastoma, melanoma, nasopharynx cancer, mesothelioma, islet cell tumor, retinoblastoma, pancreatic cancer, uterine fibroids, cervical cancer or thyroid cancer, preferably liver cancer or lung cancer.

Compared with the existing art, the present application has beneficial effects described below.

(1) In the present application, treatment/overexpression/induced overexpression of HIL-6 or L-GP130 in immune cells does not affect other immune cells, does not cause or aggravate systemic or local inflammatory reactions, and reduces the side effects of CAR-T therapy while maintaining the anti-tumor effect.

(2) The HIL-6 in the present application enhances the growth, anti-apoptosis, and cytotoxicity of CAR T cells stimulated by target cells, and meanwhile, enhances the expansion and anti-tumor effect of CAR T cells in vivo. T cells/CAR T cells, after being stimulated by HIL-6, up-regulate the expression of genes related to cell migration, memory differentiation, and IL-6/STAT3 pathway.

(3) The L-GP130 in the present application promotes the anti-tumor effect of CART cells.

BRIEF DESCRIPTION OF DRAWINGS

shows the killing capability of CAR T cells with different intracellular co-stimulatory signal transduction domains to NALM-6 in the presence/absence of overexpression of HIL-6.

DETAILED DESCRIPTION

Figure 1A:
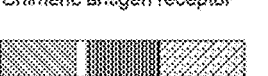
FIG. 1(a) is a schematic structural diagram of a CAR molecule.
Figure 1B:
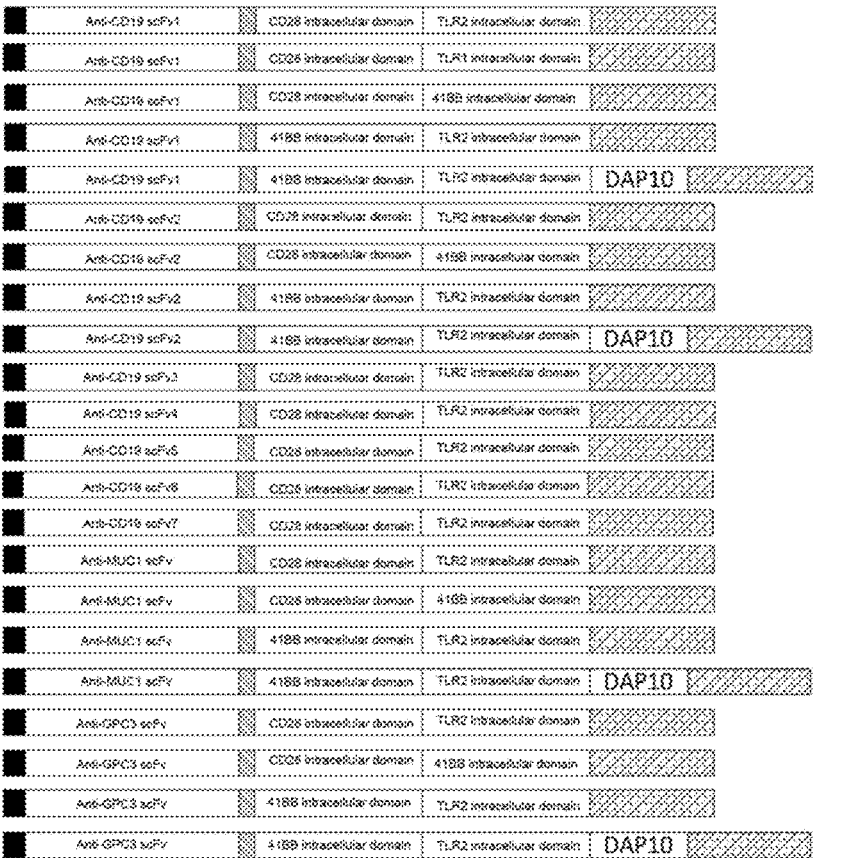
FIG. 1(b) is a schematic structural diagram of a HIL6 molecule mentioned in the specification of the present application.
Figure 1C:
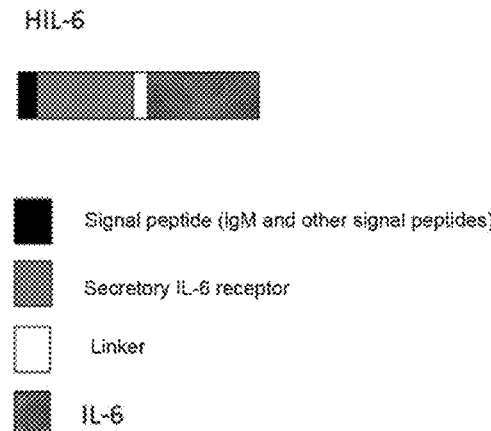
FIG. 1(c) is a schematic structural diagram of HIL-6.
Figure 1D:
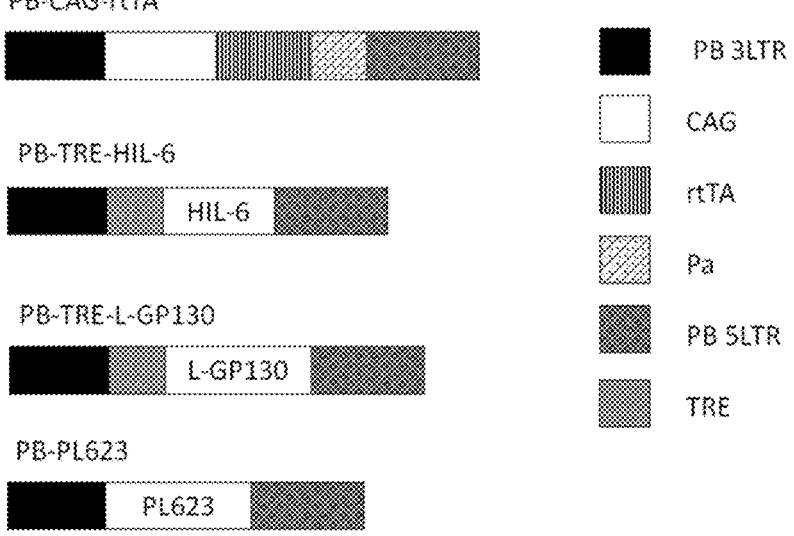
FIG. 1(d) shows a vector system in which the overexpression of HIL-6 or L-GP130 is induced by DOX.

To further elaborate on the technical means adopted and the effects achieved in the present application, the present application is described below in conjunction with the examples and drawings. It is to be understood that the specific examples as shown below are intended to illustrate but not to limit the present application.

Examples without specific techniques or conditions specified are carried out according to techniques or conditions described in the literature in the art or according to the product specification. The reagents or instruments used herein without manufacturers specified are conventional products commercially available from proper channels.

In examples of the present application, the structure of the CAR molecule is shown in FIG. 1(*a*) and FIG. 1(*b*), and the molecular structure of HIL-6 is shown in FIG. 1(*c*).

Example 1 Construction of a Constitutive Co-Expression System

Plasmid vectors pUC57-CAR-2A-HIL-6 and pUC57-CAR-2A-L-GP130, which constitutively co-expressed the CAR molecule which recognized tumor antigens and HIL-6 or L-GP130 gene, were obtained through gene synthesis.

Enzyme digestion was performed on pUC57-CAR-2A-HIL-6 and pUC57-CAR-2A-L-GP130 to obtain CAR-2A-HIL-6 and CAR-2A-L-GP130 genes. CAR-2A-HIL-6 and CAR-2A-L-GP130 genes were linked to a lentivirus vector pWPXLd (containing GFP gene) or a PB vector (containing GFP gene) to construct pWPXLd-CAR-2A-HIL-6-2A-GFP and pWPXLd-CAR-2A-L-GP130-2A-GFP or PB-CAR-2A-HIL-6-2A-GFP and PB-CAR-2A-L-GP130-2A-GFP.

In this example, the amino acid sequence of HIL-6 was as shown in SEQ ID NO: 1 or had 80% or more homology with and the same or similar activity as SEQ ID NO: 1, and the nucleic acid sequence of HIL-6 was as shown in SEQ ID NO: 2; and the amino acid sequence of L-GP130 was as shown in SEQ ID NO: 3 or had 80% or more homology with and the same or similar activity as SEQ ID NO: 3, and the nucleic acid sequence of L-GP130 was as shown in SEQ ID NO: 4.

In this example, the extracellular scFv sequence of the CAR molecule recognized any one of antigens CD19, GPC3, MUC1, Mesothelin, PSCA or HER2. The amino acid sequence of anti-CD19 scFv1 was as shown in SEQ ID NO: 5, and the nucleic acid sequence of anti-CD19 scFv1 was as shown in SEQ ID NO: 6. The amino acid sequence of anti-CD19 scFv2 was as shown in SEQ ID NO: 7. The amino acid sequence of anti-CD19 scFv3 was as shown in SEQ ID NO: 8. The amino acid sequence of anti-CD19 scFv4 was as shown in SEQ ID NO: 9. The amino acid sequence of anti-CD19 scFv5 was as shown in SEQ ID NO: 10. The amino acid sequence of anti-CD19 scFv6 was as shown in SEQ ID NO: 11. The amino acid sequence of anti-CD19 scFv7 was as shown in SEQ ID NO: 12. The amino acid sequence of anti-GPC3 scFv was as shown in SEQ ID NO: 13, and the nucleic acid sequence of anti-GPC3 scFv was as shown in SEQ ID NO: 14. The amino acid sequence of anti-MUC1 scFv was as shown in SEQ ID NO: 15, and the nucleic acid sequence of anti-MUC1 scFv was as shown in SEQ ID NO: 16. The amino acid sequence of anti-Mesothelin scFv was as shown in SEQ ID NO: 17, and the nucleic acid sequence of anti-Mesothelin scFv was as shown in SEQ ID NO: 18. The amino acid sequence of anti-PSCA scFv was as shown in SEQ ID NO: 19, and the nucleic acid sequence of anti-PSCA scFv was as shown in SEQ ID NO: 20. The amino acid sequence of anti-HER2 scFv was as shown in SEQ ID NO: 21, and the nucleic acid sequence of anti-HER2 scFv was as shown in SEQ ID NO: 22.

In this example, the intracellular co-stimulatory signal transduction sequence of the CAR molecule was any one of TLR2-CD28, TLR2-4-1BB, TLR2-DAP10*3 or CD28-41BB. The amino acid sequence of TLR2 domain was as shown in SEQ ID NO: 23, and the nucleic acid sequence of TLR2 domain was as shown in SEQ ID NO: 24. The amino acid sequence of 4-1BB was as shown in SEQ ID NO: 25, and the nucleic acid sequence of 4-1BB was as shown in SEQ ID NO: 26. The amino acid sequence of CD28 was as shown in SEQ ID NO: 27, and the nucleic acid sequence of CD28 was as shown in SEQ ID NO: 28. The amino acid sequence of DAP10*3 was as shown in SEQ ID NO: 31, and the nucleic acid sequence of DAP10*3 was as shown in SEQ ID NO: 32.

The signal peptide of the CAR molecule may be any human signal peptide, and in this example, the nucleic acid sequence of the signal peptide was as shown in SEQ ID NO: 33.

The transmembrane region of the CAR molecule may be any human signal peptide, and in this example, the nucleic acid sequence of the transmembrane region was as shown in SEQ ID NO: 34.

In this example, the nucleic acid sequence of CD3 of the CAR molecule was as shown in SEQ ID NO: 35.

In this example, the nucleic acid sequence of 2A in the vector was as shown in SEQ ID NO: 39, the nucleic acid sequence of GFP was as shown in SEQ ID NO: 40, the nucleic acid sequence of the PB vector was as shown in SEQ ID NO: 36, and the nucleic acid sequence of the lentivirus vector pWPXLd was as shown in SEQ ID NO: 44.

Example 2 Construction of a Constitutive Separate Co-Expression System

Plasmid vectors pUC57-CAR, pUC57-HIL-6, and pUC57-L-GP130, which constitutively expressed the CAR molecule which recognized tumor antigens, HIL-6 gene, and L-GP130 gene, were obtained through molecular cloning. Enzyme digestion was performed on pUC57-CAR, pUC57-HIL-6, and pUC57-L-GP130 to obtain CAR, HIL-6, and L-GP130 genes. The CAR, HIL-6, and L-GP130 genes were linked to a lentivirus vector pWPXLd (containing GFP gene) or a PB vector (containing GFP gene) to construct pWPXLd-CAR-2A-GFP, pWPXLd-HIL-6-2A-GFP and pWPXLd-L-GP130-2A-GFP or PB-CAR-2A-GFP, PB-HIL-6-2A-GFP and PB-L-GP130-2A-GFP.

In this example, the sequence information of the CAR molecule, HIL-6, L-GP130, and vectors used to construct the system was the same as that in Example 1.

Example 3 Construction of a CAR Recognition Activation-Induced Overexpression System Plasmid vectors pUC57-CAR, pUC57-NFAT repeat-IL2 promoter-HIL-6, and pUC57-NFAT repeat-IL2 promoter-L-

GP130, which expressed the CAR molecule which recognized tumor antigens, NFAT repeat (six repeats)-IL2 promoter-HIL-6 gene, and NFAT repeat-IL2 promoter-L-GP130 gene, were obtained by gene synthesis. Enzyme digestion was performed on pUC57-CAR, pUC57-NFAT repeat-IL2 promoter-HIL-6, and pUC57-NFAT repeat-IL2 promoter-L-GP130 to obtain CAR, NFAT repeat-IL2 promoter-HIL-6, and NFAT repeat-IL2 promoter-L-GP130 genes. The CAR, NFAT repeat-IL2 promoter-HIL-6, and NFAT repeat-IL2 promoter-L-GP130 genes were linked to a lentivirus vector pWPXLd (promoterless, containing a GFP gene) or a PB vector (promoterless, containing a GFP gene) to construct pWPXLd-CAR-2A-GFP, pWPXLd(promoterless)-NFAT repeat-IL2 promoter-HIL-6-2A-GFP and pWPXLd(promoterless)-NFAT repeat-IL2 promoter-L-GP130-2A-GFP, or PB-CAR-2A-GFP, PB(promoterless)-NFAT repeat-IL2 promoter-HIL-6-2A-GFP and PB(promoterless)-NFAT repeat-IL2 promoter-L-GP130-2A-GFP. This system induced HIL-6 or L-GP130 to be highly expressed after the CAR molecule recognized a tumor antigen.

In this example, the sequence information of the CAR molecule, HIL-6, and L-GP130 used to construct the system was the same as that in Example 1. In addition, the nucleic acid sequence of NFAT was as shown in SEQ ID NO: 37, the nucleic acid sequence of the IL2 promoter was as shown in SEQ ID NO: 38, the nucleic acid sequence of the PB vector (promoterless) lacked a promoter compared with the nucleic acid sequence of the PB vector as shown in SEQ ID NO: 36 and was specifically as shown in SEQ ID NO: 45, and the nucleic acid sequence of the lentivirus vector pWPXLd (promoterless) lacked a promoter compared with the nucleic acid sequence of the lentivirus vector pWPXLd as shown in SEQ ID NO: 44.

Example 4 Construction of a DOX-Induced Overexpression System

With reference to the existing art (PMID: 1990348), HIL-6 or L-GP130 gene was cloned into a PB-TRE vector by molecular cloning to construct PB-TRE-HIL-6-2A-GFP or PB-TRE-L-GP130-2A-GFP. PB-TRE-HIL-6-2A-GFP or PB-TRE-L-GP130-2A-GFP were transfected into immune cells with PB-CAG-rtTA and PB-PL623 vectors through liposomes while the CAR molecule was transduced through lentivirus. After this system was transfected into immune cells, the expression of HIL-6 or L-GP130 was induced by doxycycline (DOX) treatment, as shown in FIG. 1(*d*).

In this example, the sequence information of the CAR molecule, HIL-6, and L-GP130 used to construct the system was the same as that in Example 1. In addition, the nucleic acid sequence of PB-TRE was as shown in SEQ ID NO: 41, the nucleic acid sequence of PB-CAG-rtTA was as shown in SEQ ID NO: 42, and the nucleic acid sequence of PB-PL623 was as shown in SEQ ID NO: 43.

Example 5 Transduction and Expression of Plasmid in Immune Cells

The CAR molecule and HIL-6 or L-GP130 gene, which were constitutively expressed, expressed under the induction of DOX or expressed under the activation after the chimeric antigen receptor recognized an antigen, were integrated or transduced into immune cells by viral vector transduction, electrophoretic transfer based on a transposon subsystem or liposome-mediated plasmid transduction. Then, the immune system expressed HIL-6 or L-GP130 gene under the drive of the vector promoter so that the CAR molecule receptor was expressed on the surface of immune cells.

Exemplarily, in this example, the method of transducing T cells by lentivirus was adopted, and the specific steps are as follows.

(1) 293T cells in the logarithmic growth phase were cultured in a 150 mm culture dish (the culture medium was a DMEM high sugar medium+10% FBS (fetal bovine serum)+1% double antibiotics (100×penicillin-streptomycin mixed solution)). When the cell density reached 80% to 90%, the medium was changed to a DMEM high sugar medium+1% FBS+1% double antibiotics. After 2 hours to 6 hours, the pWPXLd-target gene-GFP constructed in Examples 1 to 4, namely the lentivirus plasmid which co-expressed/separately co-expressed/inductively expressed CAR and HIL-6/L-GP130 (pWPXLd-GFP was used as a control plasmid), pMD2.G, and psPAX2 were co-transfected into 293T cells by PEI. After 24, 48, and 72 hours after transfection, the supernatant of the culture medium was collected, and a fresh culture medium (DMEM high sugar culture medium+1% FBS+1% double antibiotics) was added. After the culture medium supernatant was collected, the culture medium supernatant was filtered by a 0.45 μM PVDF filter membrane to remove cell fragments and then placed in a refrigerator at 4° C. for later use.

(2) Isolation and purification of T cells: Mononuclear cells in blood were isolated by Ficoll density gradient method and lysed with red cell lysis buffer to remove red cells, and then T cells were sorted out by MACS Pan-T magnetic beads and diluted to $2.5 \times 10^6$ cells/ml with culture medium AIM-V supplemented with 5% FBS, 100 U/ml penicillin and 0.1 mg/ml streptomycin for later use. T cells were stimulated by magnetic beads (Miltenyi) coated with CD2, CD3, and CD28 antibodies, where the ratio of magnetic beads to T cells was 1:2, and the density of T cells was $5 \times 10^6/mL/cm^2$. T cells were cultured and stimulated for 48 hours in an incubator at 37° C. and 5% $CO_2$.

(3) Lentivirus transduction of T cells: Magnetic beads were removed. The activated T cells were centrifuged at 300 g for 5 minutes to remove supernatant, re-suspended in a fresh culture medium, added with CAR vector lentivirus at a virus dosage of MOI=10, 8 μg/ml polybrene, and 300 IU/ml IL-2 respectively, and then cultured for 24 hours in an incubator at 37° C. and 5% $CO_2$. After culture, the cells were centrifuged at 300 g for 5 minutes to remove supernatant, re-suspended in a fresh culture medium containing 300 IU/ml IL-2, and cultured in an incubator at 37° C. and 5% $CO_2$.

(4) CAR T cell expansion: The density of CAR T cells was maintained at about $1 \times 10^6/ml$, and half of the medium was changed once every 2 to 3 days. After two weeks, the number of T cells could be expanded by 100 times. The GFP-positive cells were CAR T cells successfully transduced. The GFP-positive cell percentage was detected by flow cytometry, that is, the percentage of CAR T cells or control T cells was obtained.

Example 6 Influence of HIL-6 on Growth, Anti-Apoptosis, and Cytotoxicity of CAR T Cells Anti-CD19 CART cells (the scFv sequence of the CAR molecule was, for example, anti-CD19 scFv1) were stimulated by using the NALM-6 cell line in the presence/absence of HIL-6 (5 ng/ml) treatment, and the expansion of the CAR T cells was detected 7 days later. Results are shown in FIG. 2(*a*). HIL-6 could promote the significant expansion of anti-CD19 CART cells.

Figure 2A:
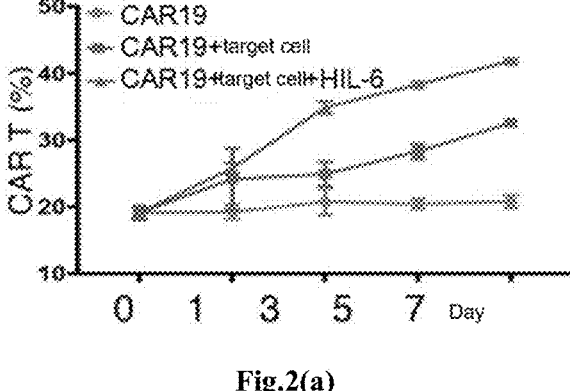
FIG. 2(a) shows the influence of HIL-6 on the expansion of CAR19 T cells when activated by tumor target cells.
Figure 2B:
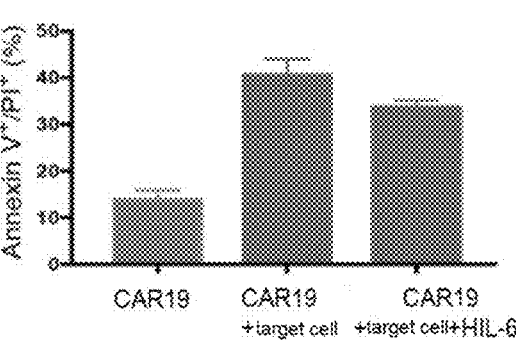
FIG. 2(b) shows the influence of HIL-6 on anti-apoptosis of CAR19 T cells when activated by tumor target cells.

The anti-CD19 CAR T cells and NALM-6 cells were co-cultured for 24 hours. Apoptosis of CAR T cells was detected by flow cytometry with Annexin V and PI staining in the presence/absence of HIL-6 (5 ng/ml). Results are shown in FIG. 2(b). HIL-6 could inhibit the apoptosis of CAR T cells activated by target cells.

Figure 2C:
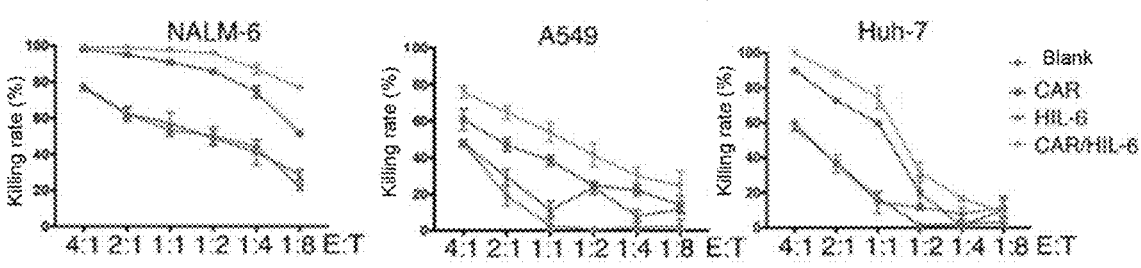
FIG. 2(c) shows the killing ability of T cells/CAR T cells to CD19+ NALM-6, MUC1+A549, and GPC3+Huh-7 in the presence/absence of overexpression of HIL-6, FIG. 2(d)

Normal T cells, anti-CD19 CAR T cells, anti-MUC1 CAR T cells, and anti-GPC3 CAR T cells were respectively mixed with target cells CD19+ NALM-6 (B-cell acute lymphoblastic leukemia cell line), MUC1+A549 (lung cancer cell line), and GPC3+ Huh-7 (liver cancer cell line) at different gradients in the case of overexpression or non-expression of HIL-6. The gradient killing effect was detected after effected cells and target cells were mixed in different proportions for 24 hours. Results are shown in FIG. 2(c).

Figure 2D:
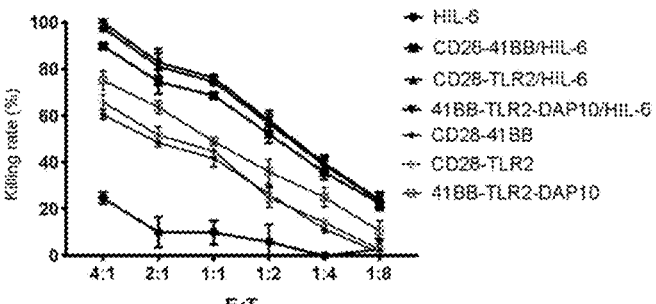
FIG. 2(e) shows the secretion of cytokines IFN-$\gamma$, TNF-$\alpha$, IL-17a, IL-6, HIL-6, and IL-2 of T cells/CAR19 cells in cytotoxicity in vitro in the presence/absence of overexpression of HIL-6.
FIG. 2(f) shows the secretion of cytokines IFN-$\gamma$, TNF-$\alpha$, IL-17a, IL-6, HIL-6, and IL-2 of T cells/MUC1 T cells in cytotoxicity in vitro in the presence/absence of overexpression of HIL-6.

Different chimeric CD19 receptor CAR T cells with a combination of intracellular co-stimulatory signal transduction domains CD28-41BB, CD28-TLR2, and CD28-TLR2-DAP10 were mixed with target cells NALM-6 (B-cell acute lymphoblastic leukemia cell line) at different gradients in the presence/absence of overexpression of HIL-6, respectively. The gradient killing effect was detected after effected cells and target cells were mixed in different proportions for 24 hours. Results are shown in FIG. 2(d).

Figure 2E:
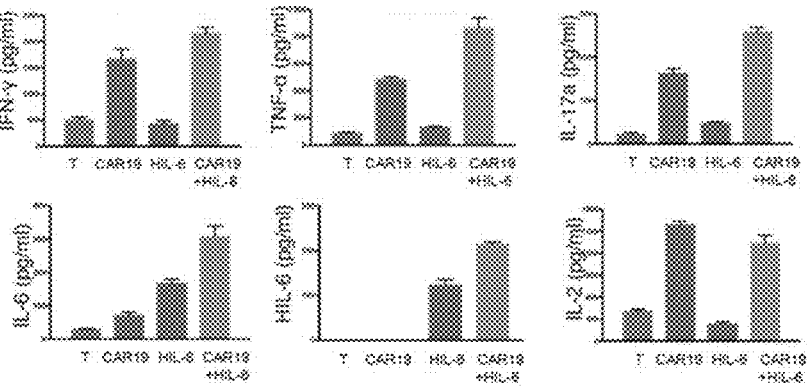
Figure 2F:
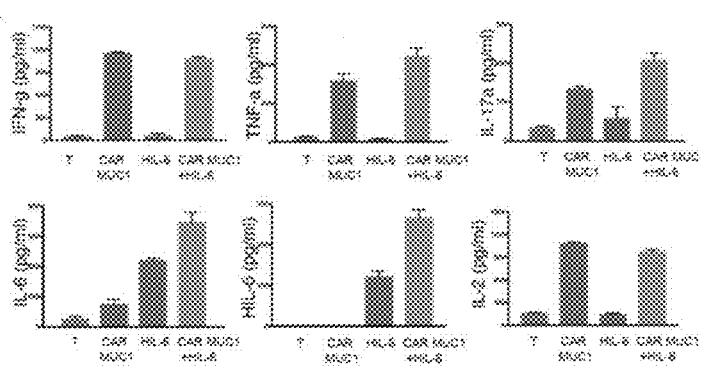

In the presence/absence of overexpression of HIL-6, the secretion of cytokines IFN-$\gamma$, TNF-$\alpha$, IL-17a, IL-6, HIL-6, and IL-2 in the supernatant obtained after normal T cells and CAR T cells targeting CD19 or CAR T cells targeting MUC1 and target cells were co-cultured for 24 hours was detected. Results are shown in FIGS. 2(e) and 2(f).

The results showed that HIL-6 could promote CAR T cells to secret tumor-killing cytokines and enhance the cytotoxicity of CAR T cells to tumor cells in vitro.

Example 7 Influence of HIL-6 on In Vivo Expansion and Anti-Tumor Effect of CAR T Cells $2\times10^5$ NALM6 cells were transplanted into NOD/SCID/IL2rg$^{-/-}$ immunodeficient mice by intravenous injection (on day 0). Then $5\times10^6$ anti-CD19 CAR T cells (the control group was T cells) were injected in the presence of overexpressing HIL-6 (the control group was the absence of overexpression of HIL-6). On day 19, peripheral blood (PB) and spleens (SP) of four groups of mice treated with T cells, anti-CD19 CAR T cells, T cells overexpressing HIL-6, and anti-CD19 CAR T cells overexpressing HIL-6 were obtained, and the ratio of human CD3+ T cells to GFP-labeled CAR T cells was detected by flow cytometry.

Figure 3A:
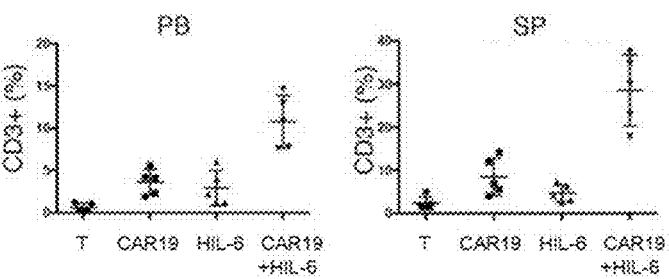
FIG. 3(a) shows the proportion and expansion of T cells in peripheral blood (PB) and spleen (SP) of mice after T cells/CAR 19 T cells were transplanted into B-cell acute lymphoblastic leukemia (NALM6 cell line) tumor-bearing mice in the presence/absence of overexpression of HIL-6.
Figure 3B:
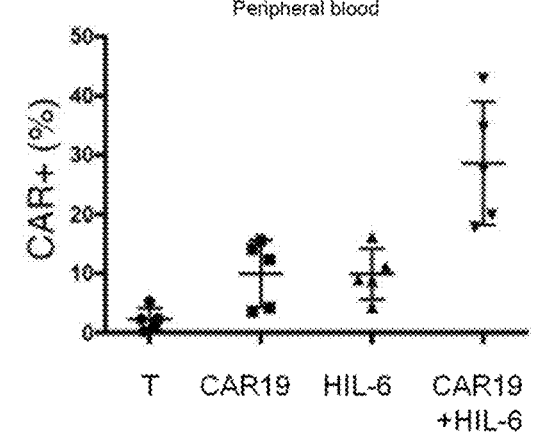
FIG. 3(b) shows the proportion and expansion of CAR T cells in peripheral blood (PB) and spleen (SP) of mice after T cells/CAR 19 T cells were transplanted into B-cell acute lymphoblastic leukemia (NALM6 cell line) tumor-bearing mice in the presence/absence of overexpression of HIL-6.
Figure 3C:
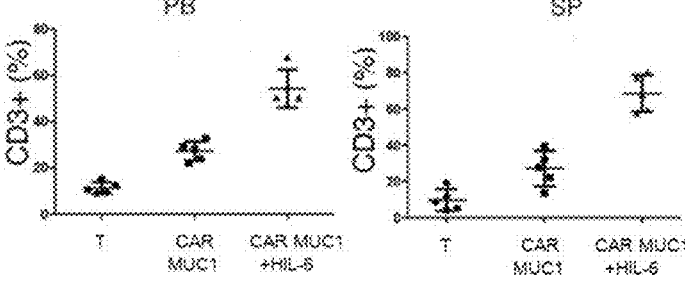
FIG. 3(c) shows the proportion of T cells in peripheral blood (PB) and spleen (SP) of mice after T cells/CAR MUC1 T cells were transplanted into lung cancer (A549 cell line) tumor-bearing mice in the presence/absence of overexpression of HIL-6, FIG. 3 (d) shows the proportion of T cells in peripheral blood (PB) and spleen (SP) of mice after T cells/CAR MUC1 T cells were transplanted into liver cancer (Huh-7 cell line) tumor-bearing mice in the presence/absence of overexpression of HIL-6.
Figure 3D:
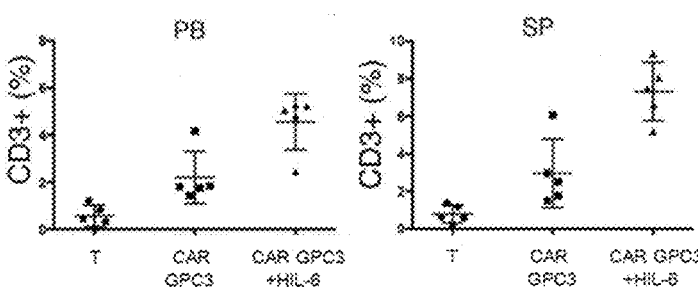
FIG. 3(e) shows the proportion of CART cells after T cells/CAR MUC1 T cells/CAR GPC3 T cells were respectively transplanted into lung cancer (A549 cell line) tumor-bearing mice and liver cancer (Huh-7 cell line) tumor-bearing mice in the presence/absence of overexpression of HIL-6.
FIG. 3(f) shows the tumor killing (tumor tissue weight) after T cells/CAR MUC1 T cells/CAR GPC3 T cells were respectively transplanted into lung cancer (A549 cell line) tumor-bearing mice and liver cancer (Huh-7 cell line) tumor-bearing mice in the presence/absence of overexpression of HIL-6.
FIG. 3(g) shows survival curves formed according to survival time of NALM6 tumor-bearing mice in the presence/absence of induced expression of HIL-6 in a case where the overexpression of HIL-6 was activated by CAR19 or Dox respectively.
Figure 3E:
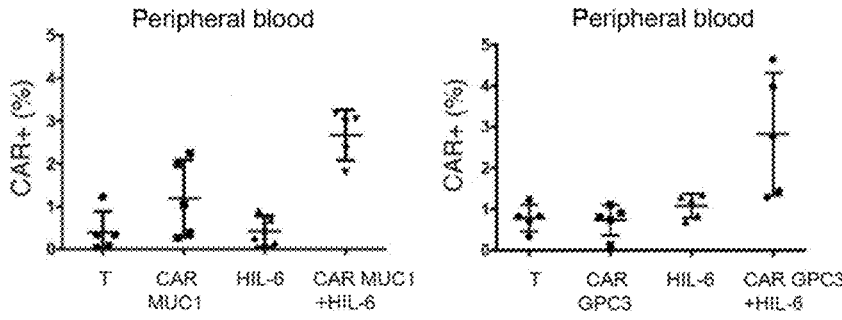
Figure 3F:
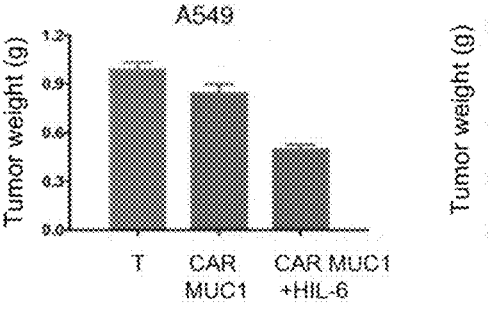
Figure 3F:
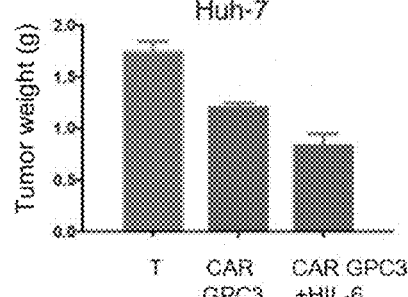

As shown in FIG. 3(a) and FIG. 3(b), T cells overexpressing HIL-6 and CAR T cells were significantly expanded in vivo, which improved the anti-tumor effect; compared with the CAR T cell group and the HIL-6 group, the proportion of CAR T cells overexpressing HIL-6 increased significantly, and the improvement effect of CAR T cells overexpressing HIL-6 was higher than the sum of improvement effects in the two groups.

$5\times10^5$ A549 cells and $5\times10^5$ Huh-7 cells were respectively transplanted into NOD/SCID/IL2rg$^{-/-}$ immunodeficient mice by subcutaneous injection (on day 0) to construct lung cancer tumor-bearing mouse models and liver cancer tumor-bearing mouse models. On day 7, $5\times10^6$ anti-MUC1 CAR T cells and $5\times10^6$ anti-GPC3 CAR T cells were respectively injected into lung cancer tumor-bearing mice and liver cancer tumor-bearing mice in the presence of overexpressing HIL-6 (the control group was the absence of overexpression of HIL-6). After about 3 to 4 weeks, tumor tissues of mice were taken, weighed, and recorded. Peripheral blood (PB) and spleens (SP) of groups of mice treated with T cells, anti-MUC1 or anti-GPC3 CAR T cells, and anti-MUC1 or anti-GPC3 CAR T cells overexpressing HIL-6 were obtained, and the ratio of human CD3+ T cells to GFP-labeled CAR T cells was detected by flow cytometry.

$2\times10^5$ NALM6 cells were transplanted into NOD/SCID/IL2rg$^{-/-}$ immunodeficient mice by intravenous injection (on day 0). Then $5\times10^6$ anti-CD19 CAR T cells (the control group was T cells) were injected. In the cases of overexpressing HIL-6 under the stimulation of CAR (CAR19 sti HIL-6 group) and overexpressing HIL-6 under the stimulation of Dox (CAR19 Dox HIL-6 group) (the control group was CAR19 T cells which were not induced to express HIL-6), six repeated experimental mice were set up in each experimental group, and the survival time of NALM6 tumor-bearing mice in different experimental groups was recorded to make survival curves.

Figure 3G:
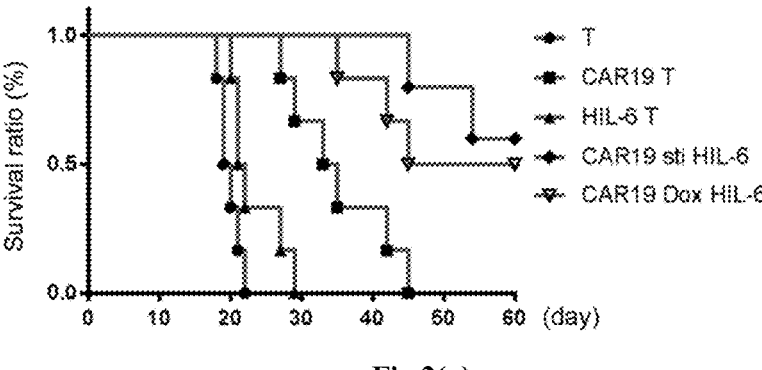

Results are shown in FIG. 3(c), FIG. 3(d), FIG. 3(e), FIG. 3 (0, and FIG. 3(g). CAR T cells overexpressing HIL-6 could significantly expanded in vivo and enhance the anti-tumor effect.

Figure 4A:
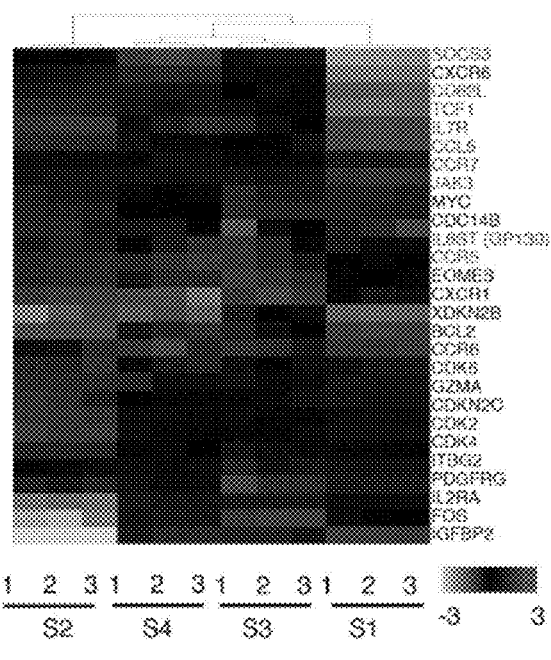
FIG. 4(a) is a thermograph of RNA sequencing results.

Example 8 Influence of HIL-6 on Genes Related to Cell Migration, Memory Differentiation, and IL-6/STAT3 Pathway in T Cells/CAR T Cells The difference of gene transcriptional expression of CAR T cells stimulated by tumor target cells and/or HIL-6 was analyzed by RNA-Seq high-throughput transcriptome sequencing. FIG. 4(a) is a thermograph of RNA sequencing results. After the CAR T cells were treated with target cells and 5 ng/mL HIL-6, some genes in the CAR T cells were up-regulated or down-regulated (fold change$\geq$2 and P value$\leq$0.05). These genes were related to T cell migration, early memory differentiation, and IL-6/GP130/STAT3 pathway.

Figure 4B:
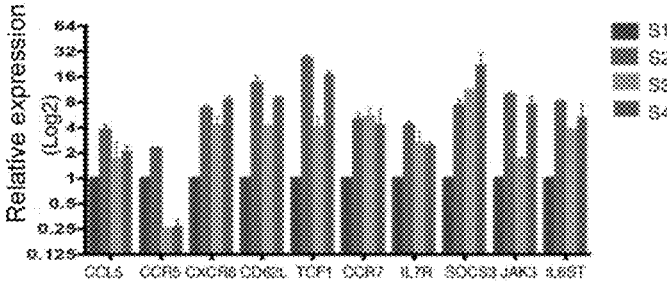
FIG. 4(b) shows the transcriptional expression of related genes in different groups of anti-CD19 CART cells detected by qRT-PCR, where S1 is CD19 CAR T cells, S2 is anti-CD19 CAR T cells treated with HIL-6, S3 is anti-CD19 CAR T cells activated by NALM6 cells, S4 is anti-CD19 CAR T cells activated by NALM6 cells and treated with HIL-6.

CAR T cells stimulated by target cells and treated by 5 ng/mL HIL-6 were detected by qRT-PCR. Results are shown in FIG. 4(b). HIL-6 could help CAR T cells to up-regulate the transcriptional expression of migration-related genes (CCL5, CCR5, and CXCR6), stage memory differentiation genes (CD62L, IL7R, CCR7, and TCF7), and IL-6/STAT3 pathway genes (SCOC3, JAK3, and IL6ST).

Figure 4C:
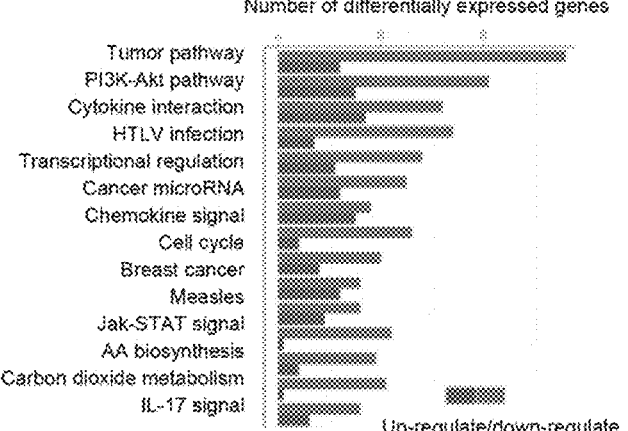
FIG. 4(c) and FIG. 4(d) show the comparison with the numbers of genes with transcriptional expression differences in signaling pathways related to T cells overexpressing HIL-6 by high-throughput transcriptome sequencing.
Figure 4D:
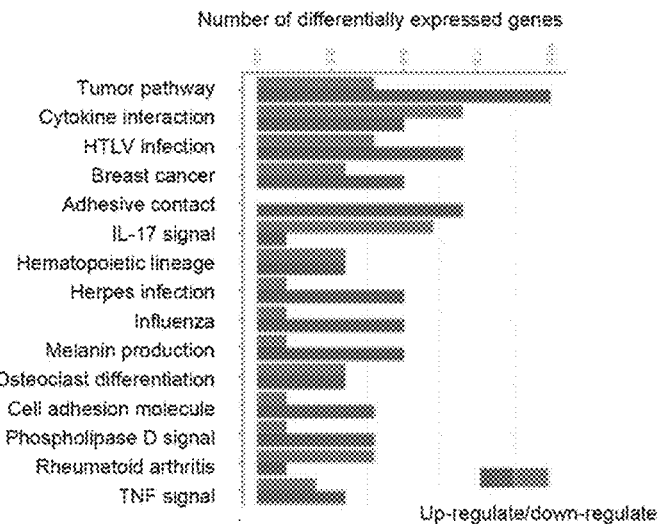

FIG. 4(c) and FIG. 4(d) show the comparison with the numbers of genes with transcriptional expression differences in signal pathways related to T cells/CAR T cells which were treated by HIL-6 (relative to T cells/CAR T cells which did not overexpress HIL-6) by high-throughput transcriptome sequencing.

Figure 5A:
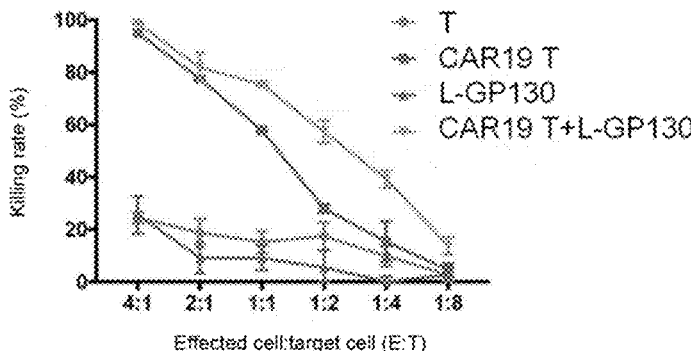
FIG. 5(a) shows the influence of overexpression of L-GP130 on cytotoxicity of CAR T cells in vitro.
Figure 5B:
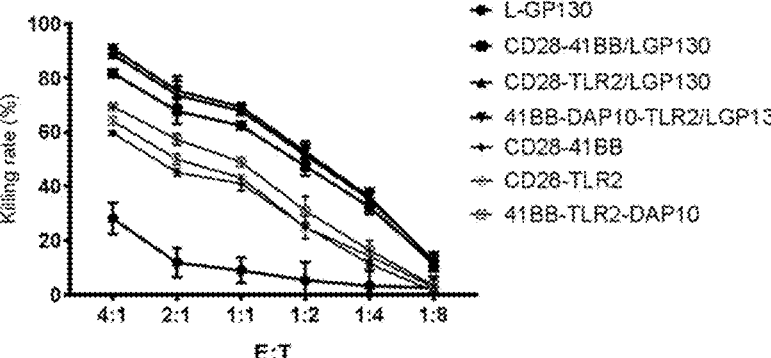
FIG. 5(b) shows the killing ability of CAR T cells with different intracellular co-stimulatory signal transduction domains to NALM-6 in the presence/absence of overexpression of L-GP130.

Example 9 Influence of L-GP130 on In Vitro Tumor-Killing Effect of CAR T Cells In the presence/absence of overexpression of L-GP130, the normal T cells and CAR T cells targeting CD19 antigen were mixed with target cells NALM-6 (B-cell acute lymphoblastic leukemia cell line) in different proportions, respectively. After 24 hours, the killing rate to tumor cells at different gradients and the secretion of cytokines IFN-$\gamma$, TNF-$\alpha$, IL-17a, IL-6, HIL-6, and IL-2 in the co-culture supernatant were detected. As shown in FIG. 5(a), L-GP130 could enhance the cytotoxicity of CAR T cells to tumor cells in vitro.

Different chimeric CD19 receptor CAR T cells with a combination of intracellular co-stimulatory signal transduction domains CD28-41BB, CD28-TLR2, and CD28-TLR2-DAP10 were mixed with target cells NALM-6 (B-cell acute lymphoblastic leukemia cell line) at different gradients in the presence/absence of overexpression of HIL-6, respectively. The gradient killing effect was detected after effected cells and target cells were mixed in different proportions for 24 hours. Results are shown in FIG. 5(d), and L-GP130 significantly improved the killing effect of CAR T cells on NALM-6.

Example 10 Influence of L-GP130 on In Vivo Anti-Tumor Effect of CART Cells

Figure 6A:
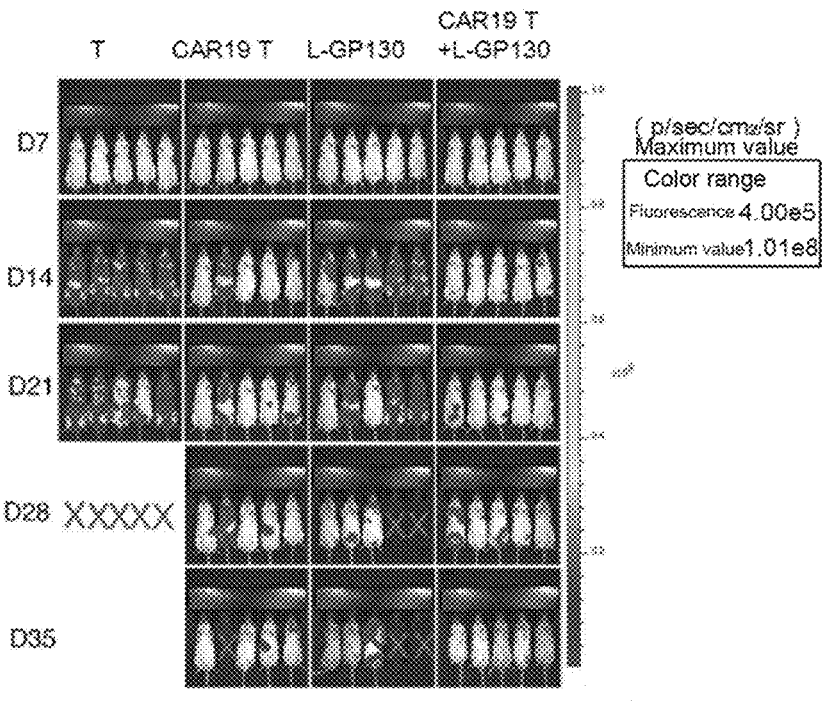
FIG. 6(a) shows the influence of overexpression of L-GP130 on tumor cell killing and inhibition of CAR T cells in vivo.
Figure 6B:
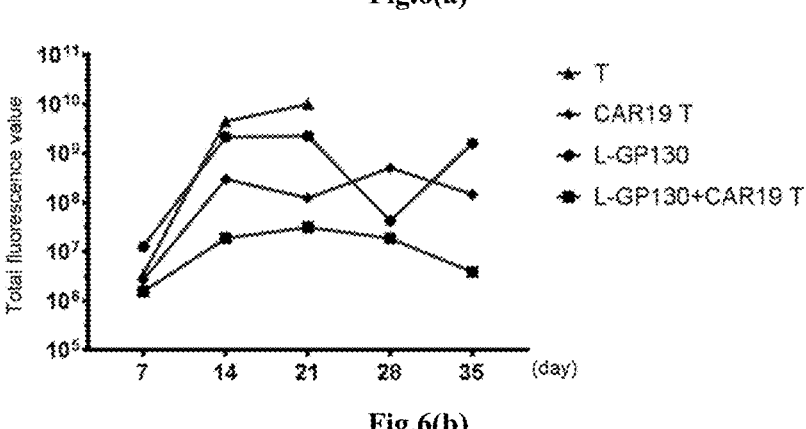
FIG. 6(b) shows the influence of overexpression of L-GP130 on the total number of target cells.
Figure 6C:
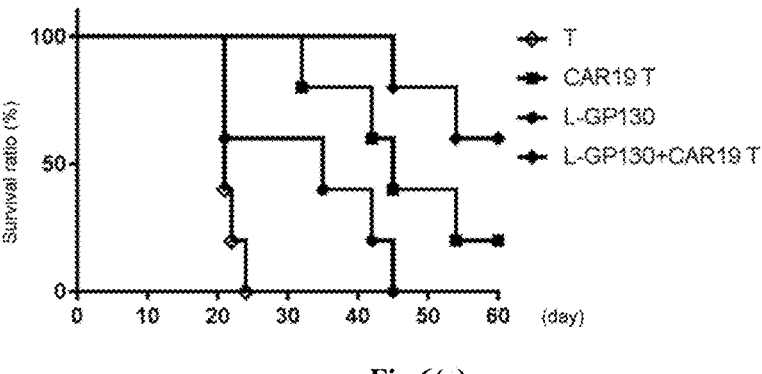
FIG. 6(c) shows the influence of overexpression of L-GP130 on the survival rate of tumor-bearing mice, FIG. 6(*d*) shows the tumor volume changes of A549 tumor-bearing mice treated by T cells and anti-MUC1 CAR T cells which overexpressed or did not overexpress L-GP130, and FIG. 6(*e*) shows the tumor volume changes of Huh-7 tumor-bearing mice treated by T cells and anti-GPC3 CAR T cells which overexpressed or did not overexpress L-GP130.

On day 0, $2\times10^5$ NALM6-GL (luciferase labeled) was transplanted into immunodeficient mice to construct leukemia tumor-bearing mouse models. On day 3, $5\times10^6$ anti-CD19 CAR T cells which overexpressed L-GP130/did not overexpress L-GP130 were injected respectively (the control group was T cells). On day 7, 14, 21, 28, and 35, luciferase substrates were injected for in vivo imaging to detect the distribution and quantification of NALM6-GL in tumor-bearing mice treated with T cells, anti-CD19 CAR T cells (CAR19 T), T cells overexpressing L-GP130, and CAR19 T cells overexpressing L-GP130. Meanwhile, the death time and survival ratio of tumor-bearing mice in different experimental groups were recorded. Results are shown in FIG. 6(a), FIG. 6(b), and FIG. 6(c). L-GP130 could enhance the in vivo anti-tumor effect of T cells and CAR T cells and prolong the survival time of tumor-bearing mice.

Figure 6D:
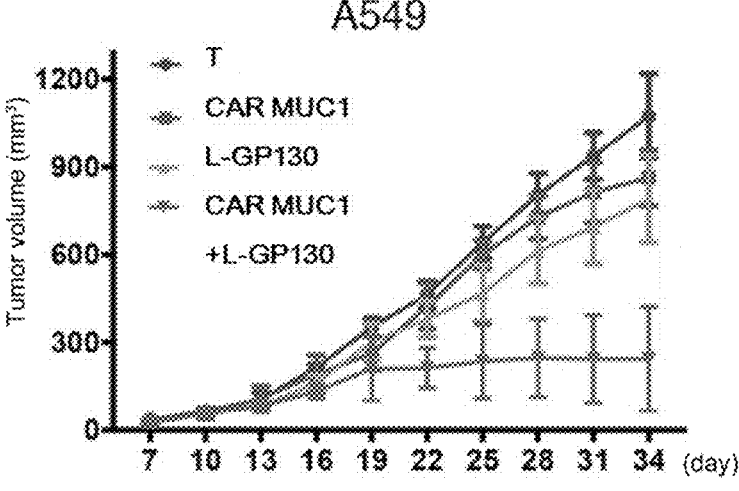

On day 0, $5\times10^5$ A549 cells were transplanted into NOD/SCID/IL2rg$^{-/-}$ immunodeficient mice by subcutaneous injection to construct lung cancer tumor-bearing mouse models. On day 5, $5\times10^6$ anti-MUC1 CAR T cells which overexpressed L-GP130/did not overexpress L-GP130 were injected into lung cancer tumor-bearing mice (the control group was T cells, and each experimental group had 5 repeated experimental mice). After day 7, the volume of lung cancer tumor tissue was measured every three days and recorded, and the curve of the tumor volume changing with time was formed. As shown in FIG. 6(d), the overexpression of L-GP130 could significantly enhance the in vivo anti-tumor effect of T cells and CART cells.

Figure 6E:
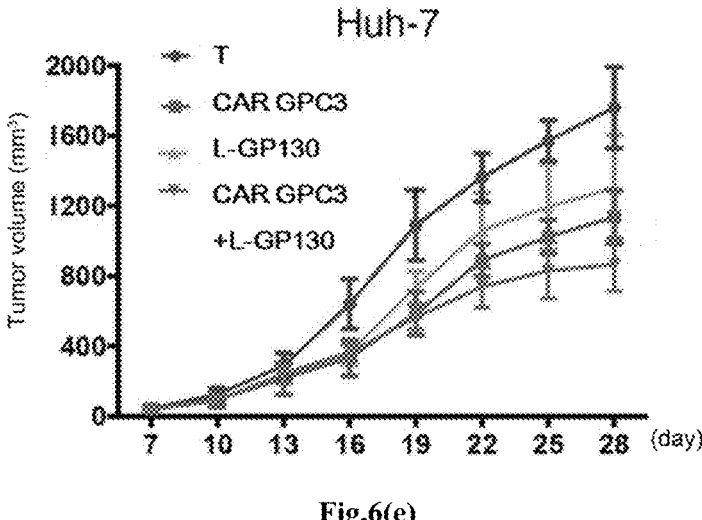

On day 0, $5\times10^5$ Huh-7 cells were transplanted into NOD/SCID/IL2rg$^{-/-}$ immunodeficient mice by subcutaneous injection to construct liver cancer tumor-bearing mouse models. On day 5, $5\times10^6$ anti-GPC3 CAR T cells which overexpressed L-GP130/did not overexpress L-GP130 were injected into liver cancer tumor-bearing mice (the control group was T cells, and each experimental group had 5 repeated experimental mice). After day 7, the volume of liver cancer tumor tissue was measured and recorded every three days, and the curve of the tumor volume changing with time was formed. As shown in FIG. 6(e), the overexpression of L-GP130 could significantly enhance the in vivo anti-tumor effect of T cells and CART cells.

In conclusion, in the present application, the treatment/overexpression/induced overexpression of HIL-6 or L-GP130 in immune cells does not affect other immune cells, does not cause or aggravate systemic or local inflammatory reactions, and reduces the side effects of CAR-T therapy while maintaining the anti-tumor effect. HIL-6 enhances the growth, anti-apoptosis, and cytotoxicity of CAR T cells stimulated by target cells and enhances the expansion and anti-tumor effect of CAR T cells in vivo. T cells/CAR T cells after being stimulated by HIL-6 up-regulates the expression of genes related to cell migration, memory differentiation, and IL-6/STAT3 pathway. L-GP130 promotes the anti-tumor effect of CART cells.

The applicant has stated that although the detailed method of the present application is described through the examples described above, the present application is not limited to the detailed method described above, which means that implementation of the present application does not necessarily depend on the detailed method described above. It should be apparent to those skilled in the art that any improvements made to the present application, equivalent replacements of raw materials of the product of the present application, additions of adjuvant ingredients to the product of the present application, and selections of specific manners, etc., all fall within the protection scope and the disclosed scope of the present application.

---

What is claimed is:

1. An immune cell overexpressing HIL-6 and L-GP130, wherein the HIL-6 has an amino acid sequence of SEQ ID NO: 1, wherein the L-GP130 has an amino acid sequence of SEQ ID NO: 3, wherein the immune cell is a T cell and wherein the T cell is modified with a CAR molecule.

2. The immune cell according to claim 1;
the T cell is selected from the group consisting of a CD4+ T cell, a CD8+ T cell, a CD4+CD8+ T cell, an NKT cell and a gamma delta ($\gamma\delta$) T cell.

3. The immune cell according to claim 1, wherein an antigen recognized by an extracellular scFv sequence of the CAR molecule comprises any one of 5T4, alpha-5 beta-1 ($\alpha5\beta1$)-integrin, 707-AP, AFP, ART-4, B7H4, B7-H3, BAGE, beta ($\beta$)-integrin/m, Bcr-abl, MN/C IX antibody, CA125, CAMEL, CAP-1, CASP-8, CD4, CD19, CD20, CD22, CD25, CDC27/m, CD30, CD33, CD52, CD56, CD80, CDK4/m, CEA, CT, Cyp-B, DAM, EGFR, ErbB3, ELF2M, EMMPRIN, EpCam, ETV6-AML1, G250, GAGE, GnT-V, Gp100, HAGE, HER-2, HLA-A*0201-R170I, HPV-E7, HSP70-2M, HST-2, hTERT, hTRT, iCE, IGF-1R, IL-2R, IL-5, KIAA0205, LAGE, LDLR/FUT, MAGE, MART-1/melan-A, MART-2/Ski, MC1R, Mesothelin, myosin/m, MUC1, MUM-1, MUM-2, MUM-3, PSCA, NA88-A, PAP, protease-3, GPC3, p190minor bcr-abl, Pml/RARR, PRAME, PSA, PSM, PSMA, RAGE, RU1, RU2, SAGE, SART-1, SART-3, survivin, TEL/AML1, PD-1, PD-L1, CTLA-4, TIM3, LAG3, TGF3, TPI/m, TRP-1, TRP-2, TRP-2/INT2, VEGF, WT1, IL-13RIN, CD123, GUCY2C, NY-Eso-1 or NY-Eso-B.

4. The immune cell according to claim 3, wherein an scFv of the anti-CD 19 CAR has an amino acid sequence of SEQ ID NO: 5 and a nucleic acid sequence of SEQ ID NO: 6 or an amino acid sequence selected from the group consisting of SEQ ID NOs: 7 to 12;
an scFv of the anti-GPC3 CAR has an amino acid sequence of SEQ ID NO: 13 and a nucleic acid sequence of SEQ ID NO: 14;
an scFv of the anti-MUC1 CAR has an amino acid sequence of SEQ ID NO: 15 and a nucleic acid sequence of SEQ ID NO: 16;
an scFv of the anti-Mesothelin has an amino acid sequence of SEQ ID NO: 17 and a nucleic acid sequence of SEQ ID NO: 18;
an scFv of the anti-PSCA has an amino acid sequence of SEQ ID NO: 19 and a nucleic acid sequence of SEQ ID NO: 20;
an scFv of the anti-HER2 has an amino acid sequence of SEQ ID NO: 21 and a nucleic acid sequence of SEQ ID NO: 22.

5. The immune cell according to claim 1, wherein the CAR molecule has an intracellular co-stimulatory signal transduction domain comprising an intracellular domain of any one of molecules of CD28, 4-1BB, TLR1, TLR2, TLR3, TLR4, TLR5, TLR6, TLR7, TLR8, TLR9, TLR10, DAP10, CD27, OX40, CD30, CD40, ICOS, lymphocyte function-associated antigen 1, CD2, CD7, LIGHT, NKG2C, NKG2D, NKp46, NKp30, NKp44, DNAM1, B7-H3, and CD83, or comprising a combination of intracellular domains of at least two of these molecules.

6. The immune cell according to claim 5, wherein the TLR2 has an amino acid sequence of SEQ ID NO: 23 and a nucleic acid sequence of SEQ ID NO: 24;
the 4-1BB has an amino acid sequence of SEQ ID NO: 25 and a nucleic acid sequence of SEQ ID NO: 26;
the CD28 has an amino acid sequence of SEQ ID NO: 27 and a nucleic acid sequence of SEQ ID NO: 28;
the TLR1 has an amino acid sequence of SEQ ID NO: 29 and a nucleic acid sequence of SEQ ID NO: 30;
the DAP10 has an amino acid sequence of SEQ ID NO: 31 and a nucleic acid sequence of SEQ ID NO: 32;
a signal peptide of the CAR molecule has a nucleic acid sequence of SEQ ID NO: 33;
a transmembrane region of the CAR molecule has a nucleic acid sequence of SEQ ID NO: 34;
CD32 of the CAR molecule has a nucleic acid sequence of SEQ ID NO: 35.

7. A method for preparing the immune cell according to claim 1, comprising overexpressing HIL-6 and L-GP130 in an immune cell, wherein the HIL-6 has an amino acid sequence of SEQ ID NO: 1, wherein the L-GP130 has an amino acid sequence of SEQ ID NO: 3, wherein the immune cell is a T cell and wherein the T cell is modified with one or two of a CAR molecule.

8. A pharmaceutical composition, comprising the immune cell according to claim 1;
the pharmaceutical composition further comprises any one or a combination of at least two of a pharmaceutically acceptable carrier, an excipient or a diluent.

9. A method for the treatment of tumors comprising: administering the immune cell of claim 1; wherein the tumor comprises CD19+B-cell acute lymphoblastic leukemia, MUC1+ lung cancer, or GPC3+ liver cancer.

10. The immune cell according to claim 1, wherein the T cell has a nucleic acid sequence of SEQ ID NO: 2.

11. The immune cell according to claim 1, wherein the T cell has a nucleic acid sequence of SEQ ID NO: 4.

* * * * *

SEQUENCE LISTING

```
<160> NUMBER OF SEQ ID NOS: 45

<210> SEQ ID NO 1
<211> LENGTH: 407
<212> TYPE: PRT
<213> ORGANISM: Artificial sequence
<220> FEATURE:
<223> OTHER INFORMATION: HIL-6

<400> SEQUENCE: 1

Pro Pro Glu Glu Pro Gln Leu Ser Cys Phe Arg Lys Ser Pro Leu Ser
1               5                   10                  15

Asn Val Val Cys Glu Trp Gly Pro Arg Ser Thr Pro Ser Leu Thr Thr
            20                  25                  30

Lys Ala Val Leu Leu Val Arg Lys Phe Gln Asn Ser Pro Ala Glu Asp
        35                  40                  45

Phe Gln Glu Pro Cys Gln Tyr Ser Gln Glu Ser Gln Lys Phe Ser Cys
    50                  55                  60

Gln Leu Ala Val Pro Glu Gly Asp Ser Ser Phe Tyr Ile Val Ser Met
65                  70                  75                  80
```

```
Cys Val Ala Ser Ser Val Gly Ser Lys Phe Ser Lys Thr Gln Thr Phe
                85                  90                  95

Gln Gly Cys Gly Ile Leu Gln Pro Asp Pro Pro Ala Asn Ile Thr Val
               100                 105                 110

Thr Ala Val Ala Arg Asn Pro Arg Trp Leu Ser Val Thr Trp Gln Asp
               115                 120                 125

Pro His Ser Trp Asn Ser Ser Phe Tyr Arg Leu Arg Phe Glu Leu Arg
           130                 135                 140

Tyr Arg Ala Glu Arg Ser Lys Thr Phe Thr Thr Trp Met Val Lys Asp
145                 150                 155                 160

Leu Gln His His Cys Val Ile His Asp Ala Trp Ser Gly Leu Arg His
               165                 170                 175

Val Val Gln Leu Arg Ala Gln Glu Glu Phe Gly Gln Gly Glu Trp Ser
               180                 185                 190

Glu Trp Ser Pro Glu Ala Met Gly Thr Pro Trp Thr Glu Ser Arg Ser
           195                 200                 205

Pro Pro Ala Arg Gly Gly Gly Ser Gly Gly Gly Ser Val Glu Pro
           210                 215                 220

Val Pro Pro Gly Glu Asp Ser Lys Asp Val Ala Ala Pro His Arg Gln
225                 230                 235                 240

Pro Leu Thr Ser Ser Glu Arg Ile Asp Lys Gln Ile Arg Tyr Ile Leu
               245                 250                 255

Asp Gly Ile Ser Ala Leu Arg Lys Glu Thr Cys Asn Lys Ser Asn Met
               260                 265                 270

Cys Glu Ser Ser Lys Glu Ala Leu Ala Glu Asn Asn Leu Asn Leu Pro
           275                 280                 285

Lys Met Ala Glu Lys Asp Gly Cys Phe Gln Ser Gly Phe Asn Glu Glu
           290                 295                 300

Thr Cys Leu Val Lys Ile Ile Thr Gly Leu Leu Glu Phe Glu Val Tyr
305                 310                 315                 320

Leu Glu Tyr Leu Gln Asn Arg Phe Glu Ser Ser Glu Glu Gln Ala Arg
               325                 330                 335

Ala Val Gln Met Ser Thr Lys Val Leu Ile Gln Phe Leu Gln Lys Lys
               340                 345                 350

Ala Lys Asn Leu Asp Ala Ile Thr Thr Pro Asp Pro Thr Thr Asn Ala
           355                 360                 365

Ser Leu Leu Thr Lys Leu Gln Ala Gln Asn Gln Trp Leu Gln Asp Met
           370                 375                 380

Thr Thr His Leu Ile Leu Arg Ser Phe Lys Glu Phe Leu Gln Ser Ser
385                 390                 395                 400

Leu Arg Ala Leu Arg Gln Met
                405
```

```
<210> SEQ ID NO 2
<211> LENGTH: 1221
<212> TYPE: DNA
<213> ORGANISM: Artificial sequence
<220> FEATURE:
<223> OTHER INFORMATION: HIL-6

<400> SEQUENCE: 2 cccccccgagg agccccagct ctcctgcttc cggaagagcc ccctcagcaa tgttgttgt       60 gagtggggtc ctcggagcac cccatccctg acgacaaagg ctgtgctctt ggtgaggaag      120
tttcagaaca gtccggccga agacttccag gagccgtgcc agtattccca ggagtcccag      180
```

-continued

```
aagttctcct gccagttagc agtcccggag ggagacagct ctttctacat agtgtccatg      240
tgcgtcgcca gtagtgtcgg gagcaagttc agcaaaactc aaacctttca gggttgtgga      300
atcttgcagc ctgatccgcc tgccaacatc acagtcactg ccgtggccag aaacccccgc      360
tggctcagtg tcacctggca agacccccac tcctggaact catctttcta cagactacgg      420
tttgagctca gatatcgggc tgaacggtca aagacattca caacatggat ggtcaaggac      480
ctccagcatc actgtgtcat ccacgacgcc tggagcggcc tgaggcacgt ggtgcagctt      540
cgtgcccagg aggagttcgg gcaaggcgag tggagcgagt ggagcccgga ggccatgggc      600
acgccttgga cagaatccag gagtcctcca gctcgcggtg gtggatcagg aggtggaggg      660
tcagtcgagc cagtaccccc aggagaagat tccaaagatg tagccgcccc cacacagacag     720 ccactcacct cttcagaacg aattgacaaa caaattcggt acatcctcga cggcatctca      780
gccctgagaa aggagacatg taacaagagt aacatgtgtg aaagcagcaa agaggcactg      840
gcagaaaaca acctgaacct tccaaagatg gctgaaaaag atggatgctt ccaatctgga      900
ttcaatgagg agacttgcct ggtgaaaatc atcactggtc ttttggagtt tgaggtatac      960
ctagagtacc tccagaacag atttgagagt agtgaggaac aagccagagc tgtgcagatg     1020
agtacaaaag tcctgatcca gttcctgcag aaaaaggcaa agaatctaga tgcaataacc     1080 accccctgacc caaccacaaa tgccagcctg ctgacgaagc tgcaggcaca gaaccagtgg     1140
ctgcaggaca tgacaactca tctcattctg cgcagcttta aggagttcct gcagtccagc     1200
ctgagggctc ttcggcaaat g                                               1221
```

<210> SEQ ID NO 3
<211> LENGTH: 344
<212> TYPE: PRT
<213> ORGANISM: Artificial sequence
<220> FEATURE:
<223> OTHER INFORMATION: L-GP130

<400> SEQUENCE: 3

```
Arg Ile Ala Arg Leu Glu Glu Lys Val Lys Thr Leu Lys Ala Gln Asn
1               5                   10                  15

Ser Glu Leu Ala Ser Thr Ala Asn Met Leu Arg Glu Gln Val Ala Gln
            20                  25                  30

Leu Lys Gln Lys Val Met Asn Ala Gln Gly Glu Ile Glu Ala Ile Val
        35                  40                  45

Val Pro Val Cys Leu Ala Phe Leu Leu Thr Thr Leu Leu Gly Val Leu
    50                  55                  60

Phe Cys Phe Asn Lys Arg Asp Leu Ile Lys Lys His Ile Trp Pro Asn
65                  70                  75                  80

Val Pro Asp Pro Ser Lys Ser His Ile Ala Gln Trp Ser Pro His Thr
                85                  90                  95

Pro Pro Arg His Asn Phe Asn Ser Lys Asp Gln Met Tyr Ser Asp Gly
            100                 105                 110

Asn Phe Thr Asp Val Ser Val Val Glu Ile Glu Ala Asn Asp Lys Lys
            115                 120                 125

Pro Phe Pro Glu Asp Leu Lys Ser Leu Asp Leu Phe Lys Lys Glu Lys
        130                 135                 140

Ile Asn Thr Glu Gly His Ser Ser Gly Ile Gly Gly Ser Ser Cys Met
145                 150                 155                 160

Ser Ser Ser Arg Pro Ser Ile Ser Ser Ser Asp Glu Asn Glu Ser Ser
                165                 170                 175
```

-continued

```
Gln Asn Thr Ser Ser Thr Val Gln Tyr Ser Thr Val Val His Ser Gly
            180                 185                 190

Tyr Arg His Gln Val Pro Ser Val Gln Val Phe Ser Arg Ser Glu Ser
        195                 200                 205

Thr Gln Pro Leu Leu Asp Ser Glu Glu Arg Pro Glu Asp Leu Gln Leu
        210                 215                 220

Val Asp His Val Asp Gly Gly Asp Gly Ile Leu Pro Arg Gln Gln Tyr
225                 230                 235                 240

Phe Lys Gln Asn Cys Ser Gln His Glu Ser Ser Pro Asp Ile Ser His
                245                 250                 255

Phe Glu Arg Ser Lys Gln Val Ser Ser Val Asn Glu Glu Asp Phe Val
            260                 265                 270

Arg Leu Lys Gln Gln Ile Ser Asp His Ile Ser Gln Ser Cys Gly Ser
        275                 280                 285

Gly Gln Met Lys Met Phe Gln Glu Val Ser Ala Ala Asp Ala Phe Gly
        290                 295                 300

Pro Gly Thr Glu Gly Gln Val Glu Arg Phe Glu Thr Val Gly Met Glu
305                 310                 315                 320

Ala Ala Thr Asp Glu Gly Met Pro Lys Ser Tyr Leu Pro Gln Thr Val
            325                 330                 335

Arg Gln Gly Gly Tyr Met Pro Gln
            340
```

<210> SEQ ID NO 4
<211> LENGTH: 1032
<212> TYPE: DNA
<213> ORGANISM: Artificial sequence
<220> FEATURE:
<223> OTHER INFORMATION: L-GP130

<400> SEQUENCE: 4

```
cgtatcgctc gtctggaaga aaaagttaaa accctgaaag ctcagaactc cgaactggct      60
tccaccgcta acatgctgcg tgaacaggtt gctcagctga acagaaagt tatgaacgct     120 caaggagaaa ttgaagccat agtcgtgcct gtttgcttag cattcctatt gacaactctt     180
ctgggagtgc tgttctgctt taataagcga gacctaatta aaaaacacat ctggcctaat     240
gttccagatc cttcaaagag tcatattgcc cagtggtcac ctcacactcc tccaaggcac     300
aattttaatt caaagatca aatgtattca gatggcaatt tcactgatgt aagtgttgtg     360
gaaatagaag caaatgacaa aaagcctttt ccagaagatc tgaaatcatt ggacctgttc     420
aaaaaggaaa aaattaatac tgaaggacac agcagtggta ttggggggtc ttcatgcatg     480
tcatcttcta ggccaagcat ttctagcagt gatgaaaatg aatcttcaca aaacacttcg     540
agcactgtcc agtattctac cgtggtacac agtggctaca gacaccaagt tccgtcagtc     600
caagtcttct caagatccga gtctacccag cccttgttag attcagagga gcggccagaa     660
gatctacaat agtagatca tgtagatggc ggtgatggta ttttgcccag gcaacagtac     720
ttcaaacaga actgcagtca gcatgaatcc agtccagata tttcacattt tgaaaggtca     780
aagcaagttt catcagtcaa tgaggaagat tttgttagac ttaaacagca gatttcagat     840
catatttcac aatcctgtgg atctgggcaa atgaaaatgt tccaggaagt ttctgcagca     900
gatgcttttg gtccaggtac tgagggacaa gtagaaagat ttgaaacagt tggcatggag     960
gctgcgactg atgaaggcat gcctaaaagt tacttaccac agactgtacg gcaaggcggc    1020
tacatgcctc ag                                                         1032
```

```
<210> SEQ ID NO 5
<211> LENGTH: 267
<212> TYPE: PRT
<213> ORGANISM: Artificial sequence
<220> FEATURE:
<223> OTHER INFORMATION: anti-CD19 CAR scFv1

<400> SEQUENCE: 5

Met Leu Leu Leu Val Thr Ser Leu Leu Leu Cys Glu Leu Pro His Pro
1               5                   10                  15

Ala Phe Leu Leu Ile Pro Asp Ile Gln Met Thr Gln Thr Thr Ser Ser
            20                  25                  30

Leu Ser Ala Ser Leu Gly Asp Arg Val Thr Ile Ser Cys Arg Ala Ser
        35                  40                  45

Gln Asp Ile Ser Lys Tyr Leu Asn Trp Tyr Gln Gln Lys Pro Asp Gly
    50                  55                  60

Thr Val Lys Leu Leu Ile Tyr His Thr Ser Arg Leu His Ser Gly Val
65                  70                  75                  80

Pro Ser Arg Phe Ser Gly Ser Gly Ser Gly Thr Asp Tyr Ser Leu Thr
                85                  90                  95

Ile Ser Asn Leu Glu Gln Glu Asp Ile Ala Thr Tyr Phe Cys Gln Gln
            100                 105                 110

Gly Asn Thr Leu Pro Tyr Thr Phe Gly Gly Gly Thr Lys Leu Glu Ile
        115                 120                 125

Thr Gly Ser Thr Ser Gly Ser Gly Lys Pro Gly Ser Gly Glu Gly Ser
    130                 135                 140

Thr Lys Gly Glu Val Lys Leu Gln Glu Ser Gly Pro Gly Leu Val Ala
145                 150                 155                 160

Pro Ser Gln Ser Leu Ser Val Thr Cys Thr Val Ser Gly Val Ser Leu
                165                 170                 175

Pro Asp Tyr Gly Val Ser Trp Ile Arg Gln Pro Pro Arg Lys Gly Leu
            180                 185                 190

Glu Trp Leu Gly Val Ile Trp Gly Ser Glu Thr Thr Tyr Tyr Asn Ser
        195                 200                 205

Ala Leu Lys Ser Arg Leu Thr Ile Ile Lys Asp Asn Ser Lys Ser Gln
    210                 215                 220

Val Phe Leu Lys Met Asn Ser Leu Gln Thr Asp Asp Thr Ala Ile Tyr
225                 230                 235                 240

Tyr Cys Ala Lys His Tyr Tyr Tyr Gly Gly Ser Tyr Ala Met Asp Tyr
                245                 250                 255

Trp Gly Gln Gly Thr Ser Val Thr Val Ser Ser
            260                 265

<210> SEQ ID NO 6
<211> LENGTH: 803
<212> TYPE: DNA
<213> ORGANISM: Artificial sequence
<220> FEATURE:
<223> OTHER INFORMATION: anti-CD19 CAR scFv1

<400> SEQUENCE: 6
atgcttctcc tggtgacaag ccttctgctc tgtgagttac cacacccagc attcctcctg      60
atcccagaca tccagatgac acagactaca tcctccctgt ctgcctctct gggagacaga     120
gtcaccatca gttgcagggc aagtcaggac attagtaaat atttaaattg gtatcagcag     180
aaaccagatg gaactgttaa actcctgatc taccatacat caagattaca ctcaggagtc     240
```

```
ccatcaaggt tcagtggcag tgggtctgga acagattatt ctctcaccat tagcaacctg          300
gagcaagaag atattgccac ttacttttgc caacagggta atacgcttcc gtacacgttc          360
ggagggggga ctaagttgga aataacaggc tccacctctg gatccggcaa gcccggatct          420 ggcgaggat ccaccaaggg cgaggtgaaa ctgcaggagt caggacctgg cctggtggcg          480
ccctcacaga gcctgtccgt cacatgcact gtctcagggg tctcattacc cgactatggt          540
gtaagctgga ttcgccagcc tccacgaaag ggtctggagt ggctgggagt aatatggggt          600
agtgaaacca catactataa ttcagctctc aaatccagac tgaccatcat caaggacaac          660
tccaagagcc aagttttctt aaaaatgaac agtctgcaaa ctgatgacac agccatttac          720
tactgtgcca acattatta ctacggtggt agctatgcta tggactactg gggtcaagga          780
acctcagtca ccgtctcctc agc                                                 803
```

<210> SEQ ID NO 7
<211> LENGTH: 250
<212> TYPE: PRT
<213> ORGANISM: Artificial sequence
<220> FEATURE:
<223> OTHER INFORMATION: anti-CD19 CAR scFv2

<400> SEQUENCE: 7

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg His
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Gln Tyr Tyr Val Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Val Glu Asp Thr Ala Val Tyr Tyr Cys
                85                  90                  95

Ala Arg Arg Ser Ile Thr Trp Tyr Gly Gly Phe Asp Ile Trp Gly Gln
            100                 105                 110

Gly Thr Met Val Thr Val Ser Ser Ala Gln Thr Thr Ala Pro Ser Val
        115                 120                 125

Tyr Pro Leu Ala Pro Gly Gly Gly Ser Gly Gly Gly Ser Gly Gly Gly
    130                 135                 140

Ser Ile Gln Met Thr Gln Ser Pro Ser Thr Leu Ser Ala Ser Val Gly
145                 150                 155                 160

Asp Arg Val Thr Ile Thr Cys Arg Ala Ser Gln Ser Ile Ser Ser Trp
                165                 170                 175

Leu Ala Trp Tyr Gln Gln Lys Pro Gly Lys Ala Pro Lys Leu Leu Ile
            180                 185                 190

Tyr Lys Ala Ser Ser Leu Glu Ser Gly Val Pro Pro Arg Phe Ser Gly
        195                 200                 205

Ser Gly Ser Gly Thr Glu Phe Thr Leu Thr Ile Ser Ser Leu Gln Pro
    210                 215                 220

Asp Asp Phe Ala Thr Tyr Tyr Cys Gln Gln Tyr Asn Ser Ala Tyr Thr
225                 230                 235                 240

Phe Gly Gln Gly Thr Lys Leu Glu Ile Lys
            245                 250
```

-continued

```
<210> SEQ ID NO 8
<211> LENGTH: 251
<212> TYPE: PRT
<213> ORGANISM: Artificial sequence
<220> FEATURE:
<223> OTHER INFORMATION: anti-CD19 CAR scFv3

<400> SEQUENCE: 8

Gln Val Gln Leu Val Glu Ser Gly Gly Gly Val Val Gln Pro Gly Arg
1               5                   10                  15

Ser Leu Arg Leu Ser Cys Glu Ala Ser Gly Phe Thr Phe Ser Arg His
            20                  25                  30

Gly Met His Trp Val Arg Gln Ala Pro Gly Lys Gly Leu Glu Trp Val
        35                  40                  45

Ala Val Ile Phe Tyr Asp Gly Ser Gln Asn Tyr Tyr Ala Asp Ser Val
    50                  55                  60

Arg Gly Arg Phe Thr Ile Ser Arg Asp Asn Ser Lys Asn Thr Leu Ser
65                  70                  75                  80

Leu Gln Met Asp Ser Leu Arg Ala Glu Asp Thr Ala Val Tyr Tyr Cys
                85                  90                  95

Ala Arg Arg Ser Ile Thr Trp Asn Gly Gly Phe Asp Ile Trp Gly Gln
            100                 105                 110

Gly Thr Met Val Thr Val Ser Pro Ala Gln Thr Thr Ala Pro Ser Val
        115                 120                 125

Tyr Pro Leu Ala Pro Gly Gly Gly Ser Gly Gly Gly Ser Gly Gly Gly
    130                 135                 140

Ser Asp Ile Gln Met Thr Gln Ser Pro Ser Thr Leu Ser Ala Ser Val
145                 150                 155                 160

Gly Asp Arg Val Thr Ile Thr Cys Arg Ala Ser Gln Ser Ile Ser Ser
                165                 170                 175

Trp Leu Ala Trp Tyr Gln Gln Lys Pro Gly Lys Ala Pro Lys Leu Leu
            180                 185                 190

Ile Tyr Lys Ala Ser Ser Leu Glu Ser Gly Val Pro Ser Arg Phe Ser
            195                 200                 205

Gly Ser Gly Ser Gly Thr Glu Phe Thr Leu Ala Ile Ser Ser Leu Gln
    210                 215                 220

Pro Asp Asp Phe Ala Thr Tyr Tyr Cys Gln Gln Tyr Asn Arg Phe Tyr
225                 230                 235                 240

Thr Phe Gly Gln Gly Thr Lys Leu Glu Ile Lys
                245                 250

<210> SEQ ID NO 9
<211> LENGTH: 251
<212> TYPE: PRT
<213> ORGANISM: Artificial sequence
<220> FEATURE:
<223> OTHER INFORMATION: anti-CD19 CAR scFv4

<400> SEQUENCE: 9

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg His
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Val Asp Ser Val
    50                  55                  60
```

-continued

```
Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Arg Arg Ser Ile Thr Trp Asp Gly Ala Phe Asp Ile Trp Gly Gln
                100                 105                 110

Gly Thr Met Val Thr Val Ser Ser Ala Gln Thr Thr Ala Pro Ser Val
            115                 120                 125

Tyr Pro Leu Ala Pro Gly Gly Gly Ser Gly Gly Gly Ser Gly Gly Gly
        130                 135                 140

Ser Asp Ile Gln Met Thr Gln Ser Pro Ser Thr Leu Ser Ala Ser Val
145                 150                 155                 160

Gly Asp Arg Val Thr Ile Ser Cys Arg Ala Ser Gln Ser Ile Ser Ser
                165                 170                 175

Trp Leu Ala Trp Tyr Gln Gln Lys Pro Gly Lys Ala Pro Lys Leu Leu
                180                 185                 190

Ile Tyr Lys Ala Ser Ser Leu Glu Ser Gly Val Pro Ser Arg Phe Ser
            195                 200                 205

Gly Ser Gly Ser Gly Thr Glu Phe Thr Leu Thr Ile Ser Ser Leu Gln
        210                 215                 220

Pro Asp Asp Phe Ala Thr Tyr Tyr Cys Gln Gln Tyr Asn Ser Ala Tyr
225                 230                 235                 240

Thr Phe Gly Gln Gly Thr Lys Leu Glu Ile Lys
                245                 250
```

```
<210> SEQ ID NO 10
<211> LENGTH: 251
<212> TYPE: PRT
<213> ORGANISM: Artificial sequence
<220> FEATURE:
<223> OTHER INFORMATION: anti-CD19 CAR scFv5

<400> SEQUENCE: 10
```

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg His
            20                  25                  30

Gly Met His Trp Val Arg Gln Ala Pro Gly Lys Gly Leu Glu Trp Val
        35                  40                  45

Ala Val Ile Tyr Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Arg Arg Ser Ile Thr Trp Asn Gly Ala Phe Asp Ile Trp Gly Gln
                100                 105                 110

Gly Thr Met Val Thr Val Ser Ser Ala Gln Thr Thr Ala Pro Ser Val
            115                 120                 125

Tyr Pro Leu Ala Pro Gly Gly Gly Ser Gly Gly Gly Ser Gly Gly Gly
        130                 135                 140

Ser Asp Ile Gln Met Thr Gln Ser Pro Ser Thr Leu Ser Ala Ser Val
145                 150                 155                 160

Gly Asp Arg Val Thr Ile Ser Cys Arg Ala Ser Gln Ser Ile Ser Ser
                165                 170                 175
```

-continued

```
Trp Leu Ala Trp Tyr Gln Gln Lys Pro Gly Lys Ala Pro Lys Leu Leu
            180                 185                 190

Ile Tyr Lys Ala Ser Ser Leu Glu Ser Gly Val Pro Ser Arg Phe Ser
        195                 200                 205

Gly Ser Gly Ser Gly Thr Glu Phe Thr Leu Thr Ile Ser Ser Leu Gln
        210                 215                 220

Pro Asp Asp Phe Ala Thr Tyr Tyr Cys Gln Gln Tyr Asn Ser Ala Tyr
225                 230                 235                 240

Thr Phe Gly Gln Gly Thr Lys Leu Glu Ile Lys
                245                 250

<210> SEQ ID NO 11
<211> LENGTH: 251
<212> TYPE: PRT
<213> ORGANISM: Artificial sequence
<220> FEATURE:
<223> OTHER INFORMATION: anti-CD19 CAR scFv6

<400> SEQUENCE: 11

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg His
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Val Asp Ser Val
        50                  55                  60

Lys Gly Arg Phe Thr Ile Ser Arg Asp Asn Ser Lys Asn Thr Leu Asp
65                  70                  75                  80

Leu Gln Met Asn Ser Leu Arg Ala Glu Asp Thr Ala Val Tyr Tyr Cys
                85                  90                  95

Ala Arg Arg Ser Ile Thr Trp Asp Gly Ala Phe Asp Ile Trp Gly Gln
            100                 105                 110

Gly Thr Met Val Thr Val Ser Ser Ala Gln Thr Thr Ala Pro Ser Val
        115                 120                 125

Tyr Pro Leu Ala Pro Gly Gly Gly Ser Gly Gly Gly Ser Gly Gly Gly
        130                 135                 140

Ser Asp Ile Gln Met Thr Gln Ser Pro Ser Thr Leu Ser Ala Ser Val
145                 150                 155                 160

Gly Asp Arg Val Thr Val Thr Cys Arg Ala Ser Gln Ser Ile Arg Ser
            165                 170                 175

Trp Leu Ala Trp Tyr Gln Gln Lys Pro Gly Lys Ala Pro Lys Leu Leu
            180                 185                 190

Ile Tyr Lys Ala Ser Ser Leu Glu Ser Gly Val Pro Ser Arg Phe Ser
        195                 200                 205

Gly Ser Gly Ser Gly Thr Glu Phe Thr Leu Thr Ile Ser Ser Leu Gln
        210                 215                 220

Pro Asp Asp Phe Ala Thr Tyr Tyr Cys Gln Gln Tyr Asn Ser Ala Tyr
225                 230                 235                 240

Thr Phe Gly Gln Gly Thr Lys Leu Glu Ile Lys
                245                 250

<210> SEQ ID NO 12
<211> LENGTH: 257
<212> TYPE: PRT
<213> ORGANISM: Artificial sequence
<220> FEATURE:
```

-continued

<223> OTHER INFORMATION: anti-CD19 CAR scFv7

<400> SEQUENCE: 12

Gln Val Gln Leu Val Glu Ser Gly Gly Gly Val Val Gln Ala Gly Arg
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
            35                  40                  45

Gly Val Ile Trp His Asp Gly Ser Ile Lys Asn Tyr Ala Asp Phe Val
        50                  55                  60

Lys Gly Arg Phe Thr Ile Ser Arg Asp Asn Ser Glu Asp Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Gln Gly Asn Tyr Tyr Gly Trp Gly Ser Tyr Lys Ala Phe
            100                 105                 110

Asp Ile Trp Gly Gln Gly Thr Met Val Thr Val Ser Ser Ala Gln Thr
            115                 120                 125

Thr Ala Pro Ser Val Tyr Pro Leu Ala Pro Gly Gly Gly Ser Gly Gly
        130                 135                 140

Gly Ser Gly Gly Gly Ser Asp Ile Gln Leu Thr Gln Ser Pro Ser Phe
145                 150                 155                 160

Leu Ser Val Phe Val Gly Asp Arg Val Thr Ile Thr Cys Arg Ala Ser
            165                 170                 175

Gln Gly Ile Ser Asn Tyr Leu Ala Trp Tyr Gln Gln Lys Pro Gly Lys
            180                 185                 190

Ala Pro Glu Leu Leu Leu Tyr Ala Thr Ser Thr Leu Gln Ser Gly Val
            195                 200                 205

Pro Ser Arg Leu Ser Gly Ser Gly Ser Gly Thr Glu Phe Thr Leu Thr
        210                 215                 220

Leu Ser Ser Leu Gln Pro Glu Asp Phe Ala Thr Tyr Tyr Cys Gln Gln
225                 230                 235                 240

Val Tyr Ser Phe Pro Tyr Thr Phe Gly Gln Gly Thr Lys Leu Glu Ile
            245                 250                 255

Lys

<210> SEQ ID NO 13
<211> LENGTH: 242
<212> TYPE: PRT
<213> ORGANISM: Artificial sequence
<220> FEATURE:
<223> OTHER INFORMATION: anti-GPC3 CAR scFv

<400> SEQUENCE: 13

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

-continued

```
Ser Arg Val Glu Ala Glu Asp Leu Gly Val Tyr Phe Cys Ser Gln Asn
            85                  90                  95

Thr His Val Pro Pro Thr Phe Gly Ser Gly Thr Lys Leu Glu Ile Lys
            100             105             110

Gly Gly Gly Gly Ser Gly Gly Gly Gly Ser Gly Gly Gly Ser Gln
        115             120             125

Val Gln Leu Gln Gln Ser Gly Ala Glu Leu Val Arg Pro Gly Ala Ser
    130             135             140

Val Lys Leu Ser Cys Lys Ala Ser Gly Tyr Thr Phe Thr Asp Tyr Glu
145             150             155             160

Met His Trp Val Lys Gln Thr Pro Val His Gly Leu Lys Trp Ile Gly
            165             170             175

Ala Leu Asp Pro Lys Thr Gly Asp Thr Ala Tyr Ser Gln Lys Phe Lys
            180             185             190

Gly Lys Ala Thr Leu Thr Ala Asp Lys Ser Ser Ser Thr Ala Tyr Met
        195             200             205

Glu Leu Arg Ser Leu Thr Ser Glu Asp Ser Ala Val Tyr Tyr Cys Thr
    210             215             220

Arg Phe Tyr Ser Tyr Thr Tyr Trp Gly Gln Gly Thr Leu Val Thr Val
225             230             235             240

Ser Ala
```

```
<210> SEQ ID NO 14
<211> LENGTH: 726
<212> TYPE: DNA
<213> ORGANISM: Artificial sequence
<220> FEATURE:
<223> OTHER INFORMATION: anti-GPC3 CAR scFv

<400> SEQUENCE: 14
gatgttgtga tgacccaaac tccactctcc ctgcctgtca gtcttggaga tcaagcctcc      60
atctcttgca gatctagtca gagccttgta cacagtaatg gaaacaccta tttacattgg     120
tacctgcaga agccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tatttctgct ctcaaaatac acatgttcct     300
cctacgttcg gatcggggac caagctggaa ataaaaggtg gaggcggttc aggcggaggt     360
ggcagcggcg gtggcgggtc gcaggttcaa ctgcagcagt ctggggctga gctggtgagg     420 cctgggggctt cagtgaagct gtcctgcaag gcttcgggct acacatttac tgactatgaa     480
atgcactggg tgaagcagac acctgtgcat ggcctaaaat ggattggagc tcttgatcct     540
aaaactggtg atactgccta cagtcagaag ttcaagggca aggccacact gactgcagac     600
aaatcctcca gcacagccta catggagctc cgcagcctga catctgagga ctctgccgtc     660
tattactgta caagattcta ctcctatact tactgggggcc aagggactct ggtcactgtc     720
tctgca                                                                726
```

```
<210> SEQ ID NO 15
<211> LENGTH: 244
<212> TYPE: PRT
<213> ORGANISM: Artificial sequence
<220> FEATURE:
<223> OTHER INFORMATION: anti-MUC1 CAR scFv

<400> SEQUENCE: 15

Asp Ile Val Val Thr Gln Glu Ser Ala Leu Thr Thr Ser Pro Gly Glu
```

-continued

```
1             5              10             15
Thr Val Thr Leu Thr Cys Arg Ser Ser Thr Gly Ala Val Thr Thr Ser
          20                 25                 30

Asn Tyr Ala Asn Trp Val Gln Glu Lys Pro Asp His Leu Phe Thr Gly
      35                 40                 45

Leu Ile Gly Gly Thr Asn Asn Arg Ala Pro Gly Val Pro Ala Arg Phe
  50                 55                 60

Ser Gly Ser Leu Ile Gly Asp Lys Ala Ala Leu Thr Ile Thr Gly Ala
65                 70                 75                 80

Gln Thr Glu Asp Glu Ala Ile Tyr Phe Cys Ala Leu Trp Tyr Ser Asn
              85                 90                 95

His Trp Val Phe Gly Gly Gly Thr Lys Leu Thr Val Leu Gly Ser Glu
          100                105                110

Gly Gly Ser Gly Ser Gly Gly Ser Gly Ser Gly Gly Ser Gly Ser Glu
          115                120                125

Val Gln Leu Gln Gln Ser Gly Gly Gly Leu Val Gln Pro Gly Gly Ser
      130                135                140

Met Lys Leu Ser Cys Val Ala Ser Gly Phe Thr Phe Ser Asn Tyr Trp
145                150                155                160

Met Asn Trp Val Arg Gln Ser Pro Glu Lys Gly Leu Glu Trp Val Ala
              165                170                175

Glu Ile Arg Leu Lys Ser Asn Asn Tyr Ala Thr His Tyr Ala Glu Ser
          180                185                190

Val Lys Gly Arg Phe Thr Ile Ser Arg Asp Asp Ser Lys Ser Ser Val
          195                200                205

Tyr Leu Gln Met Asn Asn Leu Arg Ala Glu Asp Thr Gly Ile Tyr Tyr
      210                215                220

Cys Thr Phe Gly Asn Ser Phe Ala Tyr Trp Gly Gln Gly Thr Thr Val
225                230                235                240

Thr Val Ser Ser
```

<210> SEQ ID NO 16
<211> LENGTH: 732
<212> TYPE: DNA
<213> ORGANISM: Artificial sequence
<220> FEATURE:
<223> OTHER INFORMATION: anti-MUC1 CAR scFv

<400> SEQUENCE: 16

```
gatatcgttg tgactcagga atctgcactc accacatcac ctggtgaaac agtcacactc      60
acttgtcgct caagtactgg ggctgttaca acaagtaact atgccaactg ggtccaagaa     120
aaaccagatc atttattcac tggtctaata ggtggtacca caaccgagc accaggtgtt     180 cctgccagat tctcaggctc cctgattgga gacaaggctg ccctcaccat cacaggggca     240
cagactgagg atgaggcaat atatttctgt gctctatggt acagcaacca ttgggtgttc     300
ggtggaggaa ccaaactgac tgtcctagga tccgaggtg gctcaggatc gggtggatca     360
ggctctggtg gctcaggatc ggaggtccag ctgcagcagt caggaggagg cttggtgcaa     420
cctggaggat ccatgaaact ctcctgtgtt gcctctggat tcactttcag taactactgg     480
atgaactggg tccgccagtc tccagagaag gggcttgagt gggttgctga aattagattg     540
aaatctaata ttatgcaac acattatgcg gagtctgtga agggaggtt caccatctca     600 agagatgatt ccaaaagtag tgtctacctg caaatgaaca acttaagagc tgaagacact     660
ggcatttatt actgtacctt tggtaactcc tttgcttact ggggccaagg gaccacggtc     720
```

-continued

```
accgtctcct ca                                                    732

<210> SEQ ID NO 17
<211> LENGTH: 267
<212> TYPE: PRT
<213> ORGANISM: Artificial sequence
<220> FEATURE:
<223> OTHER INFORMATION: anti-Mesothelin scFv

<400> SEQUENCE: 17

Ser Gln Val Gln Leu Gln Gln Ser Gly Pro Gly Leu Val Thr Pro Ser
1               5                   10                  15

Gln Thr Leu Ser Leu Thr Cys Ala Ile Ser Gly Asp Ser Val Ser Ser
            20                  25                  30

Asn Ser Ala Thr Trp Asn Trp Ile Arg Gln Ser Pro Ser Arg Gly Leu
        35                  40                  45

Glu Trp Leu Gly Arg Thr Tyr Tyr Arg Ser Lys Trp Tyr Asn Asp Tyr
    50                  55                  60

Ala Val Ser Val Lys Ser Arg Met Ser Ile Asn Pro Asp Thr Ser Lys
65                  70                  75                  80

Asn Gln Phe Ser Leu Gln Leu Asn Ser Val Thr Pro Glu Asp Thr Ala
                85                  90                  95

Val Tyr Tyr Cys Ala Arg Gly Met Met Thr Tyr Tyr Tyr Gly Met Asp
            100                 105                 110

Val Trp Gly Gln Gly Thr Thr Val Thr Val Ser Ser Gly Ile Leu Gly
        115                 120                 125

Ser Gly Gly Gly Gly Ser Gly Gly Gly Gly Ser Gly Gly Gly Gly Ser
        130                 135                 140

Gln Pro Val Leu Thr Gln Ser Ser Ser Leu Ser Ala Ser Pro Gly Ala
145                 150                 155                 160

Ser Ala Ser Leu Thr Cys Thr Leu Arg Ser Gly Ile Asn Val Gly Pro
                165                 170                 175

Tyr Arg Ile Tyr Trp Tyr Gln Gln Lys Pro Gly Ser Pro Pro Gln Tyr
            180                 185                 190

Leu Leu Asn Tyr Lys Ser Asp Ser Asp Lys Gln Gln Gly Ser Gly Val
            195                 200                 205

Pro Ser Arg Phe Ser Gly Ser Lys Asp Ala Ser Ala Asn Ala Gly Val
        210                 215                 220

Leu Leu Ile Ser Gly Leu Arg Ser Glu Asp Glu Ala Asp Tyr Tyr Cys
225                 230                 235                 240

Met Ile Trp His Ser Ser Ala Ala Val Phe Gly Gly Gly Thr Gln Leu
                245                 250                 255

Thr Val Leu Ser Gly Ile Leu Glu Gln Gln Gly
            260                 265

<210> SEQ ID NO 18
<211> LENGTH: 801
<212> TYPE: DNA
<213> ORGANISM: Artificial sequence
<220> FEATURE:
<223> OTHER INFORMATION: anti-Mesothelin scFv

<400> SEQUENCE: 18
agccaggtac agctgcagca gtcaggtcca ggactcgtga cgccctcgca gaccctctca    60
ctcacctgtg ccatctccgg ggacagtgtc tctagcaaca gtgctacttg gaactggatc   120
aggcagtccc catcgagagg ccttgagtgg ctgggaagga catactacag gtccaagtgg   180
```

```
tataacgact atgcagtatc tgtgaaaagt cgaatgagca tcaacccaga cacatccaag    240
aaccagttct ccctgcagct gaactctgtg actcccgagg acacggctgt gtattactgt    300
gcaagaggaa tgatgactta ctattacggt atggacgtct ggggccaagg gaccacggtc    360
accgtctcct caggaattct aggatccggt ggcggtggca gcggcggtgg tggttccgga    420
ggcggcggtt ctcagcctgt gctgactcag tcgtcttccc tctctgcatc tcctggagca    480
tcagccagtc tcacctgcac cttgcgcagt ggcatcaatg ttggtcccta caggatatac    540
tggtaccagc agaagccagg gagtcctccc cagtatctcc tgaactacaa atcagactca    600
gataagcagc agggctctgg agtccccagc cgcttctctg atccaaaga tgcttcggcc    660 aatgcagggg ttttactcat ctctgggctc cggtctgagg atgaggctga ctattactgt    720
atgatttggc acagcagcgc tgctgtgttc ggaggaggca cccaactgac cgtcctctcc    780
ggaattctag aacaacaggg t    801
```

```
<210> SEQ ID NO 19
<211> LENGTH: 250
<212> TYPE: PRT
<213> ORGANISM: Artificial sequence
<220> FEATURE:
<223> OTHER INFORMATION: anti-PSCA scFv

<400> SEQUENCE: 19

Asp Ile Gln Leu Thr Gln Ser Pro Ser Ser Leu Ser Ala Ser Val Gly
1               5                   10                  15

Asp Arg Val Thr Ile Thr Cys Ser Ala Ser Ser Ser Val Arg Phe Ile
            20                  25                  30

His Trp Tyr Gln Gln Lys Pro Gly Lys Ala Pro Lys Arg Leu Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Phe Thr Leu Thr Ile Ser Ser Leu Gln Pro Glu
65                  70                  75                  80

Asp Phe Ala Thr Tyr Tyr Cys Gln Gln Trp Ser Ser Ser Pro Phe Thr
                85                  90                  95

Phe Gly Gln Gly Thr Lys Val Glu Ile Lys Gly Ser Thr Ser Gly Gly
            100                 105                 110

Gly Ser Gly Gly Gly Ser Gly Gly Gly Ser Ser Glu Val Gln Leu
        115                 120                 125

Val Glu Ser Gly Gly Gly Leu Val Gln Pro Gly Gly Ser Leu Arg Leu
    130                 135                 140

Ser Cys Ala Ala Ser Gly Phe Asn Ile Lys Asp Tyr Tyr Ile His Trp
145                 150                 155                 160

Val Arg Gln Ala Pro Gly Lys Gly Leu Glu Trp Val Ala Trp Ile Asp
            165                 170                 175

Pro Glu Asn Gly Asp Thr Glu Phe Val Pro Lys Phe Gln Gly Arg Ala
            180                 185                 190

Thr Ile Ser Ala Asp Thr Ser Lys Asn Thr Ala Tyr Leu Gln Met Asn
        195                 200                 205

Ser Leu Arg Ala Glu Asp Thr Ala Val Tyr Tyr Cys Lys Thr Gly Gly
    210                 215                 220

Phe Trp Gly Gln Gly Thr Leu Val Thr Val Ser Ser Glu Pro Lys Ser
225                 230                 235                 240

Cys Asp Lys Thr His Thr Cys Pro Pro Cys
```

-continued

```
                  245              250

<210> SEQ ID NO 20
<211> LENGTH: 750
<212> TYPE: DNA
<213> ORGANISM: Artificial sequence
<220> FEATURE:
<223> OTHER INFORMATION: anti-PSCA scFv

<400> SEQUENCE: 20
gacattcagc tgacccaatc tccaagctct ttgtccgcct ctgtggggga tagggtcacc      60
atcacctgca gtgccagttc aagtgtaaga ttcattcact ggtaccagca gaaaccagga     120
aaagctccca aaagactcat ctatgacaca tccaaactgg cttctggcgt cccttctagg     180
ttcagtggct ccgggtctgg gacagacttc accctcacca ttagcagtct gcagccggaa     240
gatttcgcca cctattactg tcagcagtgg agtagtagcc cattcacgtt cggacagggg     300
accaaggtgg agataaaagg cagtactagc ggcggtggct ccggaggcgg ctccggaggt     360
ggcggcagct cagaggttca gctggtggag tctggggggtg gccttgtgca gccagggggc     420
tcactccgtt tgtcctgcgc agcttctggc ttcaacatta agactacta tatacactgg      480 gtgcgtcagg cccctggtaa gggcctggaa tgggttgcat ggattgatcc tgagaatggt     540
gacactgaat ttgtcccgaa gttccagggc cgtgccacta taagcgcaga cacatccaaa     600
aacacagcct acctgcagat gaacagcctg cgtgctgagg acactgccgt ctattattgt     660
aaaacggggg ggttctgggg tcaaggaacc ctggtcaccg tctcgagcga gcccaaatct     720
tgtgacaaaa ctcacacatg cccaccgtgc                                     750

<210> SEQ ID NO 21
<211> LENGTH: 229
<212> TYPE: PRT
<213> ORGANISM: Artificial sequence
<220> FEATURE:
<223> OTHER INFORMATION: anti-HER2 scFv

<400> SEQUENCE: 21

Ile Leu Met Thr Gln Ser Pro Ala Ile Met Ser Ala Ile Met Ser Ala
1               5                  10                  15

Ser Pro Gly Glu Lys Val Thr Met Thr Cys Ser Ala Ser Ser Ser Val
            20                  25                  30

Ser Tyr Met His Trp Tyr Gln Gln Lys Ser Gly Thr Ser Pro Lys Arg
        35                  40                  45

Trp Ile Tyr Asp Thr Ser Lys Leu Ala Ser Gly Val Pro Ala Arg Phe
    50                  55                  60

Ser Gly Ser Gly Ser Gly Thr Ser Tyr Ser Leu Thr Ile Ser Ser Met
65                  70                  75                  80

Glu Ala Glu Asp Ala Ala Thr Tyr Tyr Cys Gln Gln Trp Ser Ser Asn
                85                  90                  95

Pro Leu Thr Phe Gly Ala Gly Thr Lys Leu Glu Ile Lys Gly Gly Ser
            100                 105                 110

Gly Ser Gly Gly Ser Gly Ser Gly Gly Ser Gly Ser Gly Pro Gly Leu
        115                 120                 125

Ala Ala Pro Ser Gln Ser Leu Ser Ile Thr Cys Thr Val Ser Gly Phe
        130                 135                 140

Ser Leu Thr Ser Tyr Val Ile Ser Trp Val Arg Gln Pro Pro Gly Lys
145                 150                 155                 160

Gly Leu Glu Trp Leu Gly Val Ile Trp Thr Gly Gly Gly Thr Asn Tyr
```

```
              165              170              175
Asn Ser Ala Leu Lys Ser Arg Leu Ser Ile Ser Lys Asp Asn Ser Lys
             180              185              190
Ser Gln Val Ser Leu Lys Met Asn Ser Leu Gln Thr Asp Asp Thr Ala
         195              200              205
Arg Tyr Tyr Cys Ala Ser Leu Ser Tyr Asp Gly Phe Asp Tyr Trp Gly
         210              215              220
Gln Gly Thr Thr Val
225

<210> SEQ ID NO 22
<211> LENGTH: 689
<212> TYPE: DNA
<213> ORGANISM: Artificial sequence
<220> FEATURE:
<223> OTHER INFORMATION: anti-HER2 scFv

<400> SEQUENCE: 22
attctgatga cccagtctcc agcaatcatg tctgcaatca tgtctgcatc tccaggggag        60
aaggtcacca tgacctgcag tgccagctca agtgtaagtt acatgcactg gtaccagcag       120
aagtcaggca cctcccccaa agatggatt tatgacacac ccaaactggc ttctggagtc        180
cctgctcgct tcagtggcag tgggtctggg acctcttact ctctcacaat cagcagcatg       240
gaggctgaag atgctgccac ttattactgc cagcagtgga gtagtaaccc gctcacgttc       300
ggtgctggga ccaagctgga aataaaaggt ggctcaggat cgggtggatc aggctctggt       360
ggctcaggat cgggacctgg cctggcggcg ccctcacaga gcctgtccat cacatgcact       420
gtctctgggt tctcattaac cagctatgtt ataagttggg ttcgccagcc accaggaaag       480
ggtctggagt ggcttggagt aatatggact ggtggaggca caaattataa ttcagctctc       540
aaatccagac tgagcatcag caaagacaac tccaagagtc aagtttcctt aaaaatgaac       600
agtctgcaaa ctgatgacac agccaggtac tactgtgcca gcctttccta tgatggtttc       660
gactactggg gccaagggac cacggtcac                                        689

<210> SEQ ID NO 23
<211> LENGTH: 159
<212> TYPE: PRT
<213> ORGANISM: Artificial sequence
<220> FEATURE:
<223> OTHER INFORMATION: TLR2

<400> SEQUENCE: 23

Gln Ala Lys Arg Lys Pro Arg Lys Ala Pro Ser Arg Asn Ile Cys Tyr
1               5               10               15
Asp Ala Phe Val Ser Tyr Ser Glu Arg Asp Ala Tyr Trp Val Glu Asn
             20               25               30
Leu Met Val Gln Glu Leu Glu Asn Phe Asn Pro Pro Phe Lys Leu Cys
         35               40               45
Leu His Lys Arg Asp Phe Ile Pro Gly Lys Trp Ile Ile Asp Asn Ile
         50               55               60
Ile Asp Ser Ile Glu Lys Ser His Lys Thr Val Phe Val Leu Ser Glu
65               70               75               80
Asn Phe Val Lys Ser Glu Trp Cys Lys Tyr Glu Leu Asp Phe Ser His
                 85               90               95
Phe Arg Leu Phe Asp Glu Asn Asn Asp Ala Ala Ile Leu Ile Leu Leu
             100              105              110
```

-continued

```
Glu Pro Ile Glu Lys Lys Ala Ile Pro Gln Arg Phe Cys Lys Leu Arg
        115                 120                 125

Lys Ile Met Asn Thr Lys Thr Tyr Leu Glu Trp Pro Met Asp Glu Ala
    130                 135                 140

Gln Arg Glu Gly Phe Trp Val Asn Leu Arg Ala Ala Ile Lys Ser
145                 150                 155

<210> SEQ ID NO 24
<211> LENGTH: 477
<212> TYPE: DNA
<213> ORGANISM: Artificial sequence
<220> FEATURE:
<223> OTHER INFORMATION: TLR2

<400> SEQUENCE: 24
caggccaaaa ggaagcccag gaaagctccc agcaggaaca tctgctatga tgcatttgtt      60
tcttacagtg agcgggatgc ctactgggtg gagaacctta tggtccagga gctggagaac     120
ttcaatcccc ccttcaagtt gtgtcttcat aagcgggact tcattcctgg caagtggatc     180
attgacaata tcattgactc cattgaaaag agccacaaaa ctgtctttgt gctttctgaa     240
aactttgtga gagtgagtg gtgcaagtat gaactggact tctcccattt ccgtcttttt     300
gatgagaaca tgatgctgc cattctcatt cttctggagc ccattgagaa aaaagccatt     360
ccccagcgct tctgcaagct gcggaagata tgaacacca gacctacct ggagtggccc     420 atggacgagg ctcagcggga aggattttgg gtaaatctga gagctgcgat aaagtcc     477

<210> SEQ ID NO 25
<211> LENGTH: 42
<212> TYPE: PRT
<213> ORGANISM: Artificial sequence
<220> FEATURE:
<223> OTHER INFORMATION: 4-1BB

<400> SEQUENCE: 25

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 26
<211> LENGTH: 126
<212> TYPE: DNA
<213> ORGANISM: Artificial sequence
<220> FEATURE:
<223> OTHER INFORMATION: 4-1BB

<400> SEQUENCE: 26
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                126

<210> SEQ ID NO 27
<211> LENGTH: 107
<212> TYPE: PRT
<213> ORGANISM: Artificial sequence
<220> FEATURE:
<223> OTHER INFORMATION: CD28

<400> SEQUENCE: 27
```

```
Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val Arg Ser Lys Arg Ser Arg Leu Leu His Ser Asp Tyr Met Asn
65                  70                  75                  80

Met Thr Pro Arg Arg Pro Gly Pro Thr Arg Lys His Tyr Gln Pro Tyr
                85                  90                  95

Ala Pro Pro Arg Asp Phe Ala Ala Tyr Arg Ser
            100                 105
```

```
<210> SEQ ID NO 28
<211> LENGTH: 321
<212> TYPE: DNA
<213> ORGANISM: Artificial sequence
<220> FEATURE:
<223> OTHER INFORMATION: CD28

<400> SEQUENCE: 28
attgaagtta tgtatcctcc tccttaccta gacaatgaga agagcaatgg aaccattatc      60
catgtgaaag ggaaacacct ttgtccaagt cccctatttc ccggaccttc taagcccttt     120
tgggtgctgg tggtggttgg gggagtcctg gcttgctata gcttgctagt aacagtggcc     180
tttattattt tctgggtgag gagtaagagg agcaggctcc tgcacagtga ctacatgaac     240
atgactcccc gccgccccgg gcccacccgc aagcattacc agccctatgc cccaccacgc     300
gacttcgcag cctatcgctc c                                              321
```

```
<210> SEQ ID NO 29
<211> LENGTH: 162
<212> TYPE: PRT
<213> ORGANISM: Artificial sequence
<220> FEATURE:
<223> OTHER INFORMATION: TLR1

<400> SEQUENCE: 29

Asn Ile Pro Leu Glu Glu Leu Gln Arg Asn Leu Gln Phe His Ala Phe
1               5                   10                  15

Ile Ser Tyr Ser Gly His Asp Ser Phe Trp Val Lys Asn Glu Leu Leu
            20                  25                  30

Pro Asn Leu Glu Lys Glu Gly Met Gln Ile Cys Leu His Glu Arg Asn
        35                  40                  45

Phe Val Pro Gly Lys Ser Ile Val Glu Asn Ile Ile Thr Cys Ile Glu
    50                  55                  60

Lys Ser Tyr Lys Ser Ile Phe Val Leu Ser Pro Asn Phe Val Gln Ser
65                  70                  75                  80

Glu Trp Cys His Tyr Glu Leu Tyr Phe Ala His His Asn Leu Phe His
                85                  90                  95

Glu Gly Ser Asn Ser Leu Ile Leu Ile Leu Leu Glu Pro Ile Pro Gln
            100                 105                 110

Tyr Ser Ile Pro Ser Ser Tyr His Lys Leu Lys Ser Leu Met Ala Arg
        115                 120                 125

Arg Thr Tyr Leu Glu Trp Pro Lys Glu Lys Ser Lys Arg Gly Leu Phe
```

```
              130              135              140
Trp Ala Asn Leu Arg Ala Ala Ile Asn Ile Lys Leu Thr Glu Gln Ala
145              150              155              160

Lys Lys

<210> SEQ ID NO 30
<211> LENGTH: 486
<212> TYPE: DNA
<213> ORGANISM: Artificial sequence
<220> FEATURE:
<223> OTHER INFORMATION: TLR1

<400> SEQUENCE: 30
aacataccct tagaagaact ccaaagaaat ctccagtttc atgcatttat ttcatatagt      60
gggcacgatt ctttctgggt gaagaatgaa ttattgccaa acctagagaa agaaggtatg     120
cagatttgcc ttcatgagag aaactttgtt cctggcaaga gcattgtgga aaatatcatc     180
acctgcattg agaagagtta caagtccatc tttgttttgt ctcccaactt tgtccagagt     240
gaatggtgcc attatgaact ctactttgcc catcacaatc tctttcatga aggatctaat     300
agcttaatcc tgatcttgct ggaacccatt ccgcagtact ccattcctag cagttatcac     360
aagctcaaaa gtctcatggc caggaggact tatttggaat ggcccaagga aaagagcaaa     420
cgtggccttt tttgggctaa cttaagggca gccattaata ttaagctgac agagcaagca     480
aagaaa                                                                486

<210> SEQ ID NO 31
<211> LENGTH: 24
<212> TYPE: PRT
<213> ORGANISM: Artificial sequence
<220> FEATURE:
<223> OTHER INFORMATION: DAP10

<400> SEQUENCE: 31

Leu Cys Ala Arg Pro Arg Arg Ser Pro Ala Gln Glu Asp Gly Lys Val
1               5                10               15

Tyr Ile Asn Met Pro Gly Arg Gly
            20

<210> SEQ ID NO 32
<211> LENGTH: 72
<212> TYPE: DNA
<213> ORGANISM: Artificial sequence
<220> FEATURE:
<223> OTHER INFORMATION: DAP10

<400> SEQUENCE: 32
ctgtgcgcac gcccacgccg cagccccgcc caagaagatg gcaaagtcta catcaacatg      60
ccaggcaggg gc                                                          72

<210> SEQ ID NO 33
<211> LENGTH: 64
<212> TYPE: DNA
<213> ORGANISM: Artificial sequence
<220> FEATURE:
<223> OTHER INFORMATION: Signal peptide

<400> SEQUENCE: 33
aaacatggag acagacacac tcctgctatg ggtgctgctg ctctgggttc caggttccac      60
cggt                                                                   64
```

<210> SEQ ID NO 34
<211> LENGTH: 81
<212> TYPE: DNA
<213> ORGANISM: Artificial sequence
<220> FEATURE:
<223> OTHER INFORMATION: transmembrane region

<400> SEQUENCE: 34
ttttgggtgc tggtggtggt tgggggagtc ctggcttgct atagcttgct agtaacagtg      60
gcctttatta ttttctgggt g                                                81

<210> SEQ ID NO 35
<211> LENGTH: 336
<212> TYPE: DNA
<213> ORGANISM: Artificial sequence
<220> FEATURE:
<223> OTHER INFORMATION: CD3 Zeta

<400> SEQUENCE: 35
agagtgaagt tcagcaggag cgcagacgcc cccgcgtacc agcagggcca gaaccagctc      60
tataacgagc tcaatctagg acgaagagag gagtacgatg ttttggacaa gagacgtggc     120
cgggaccctg atggggggg aaagccgaga aggaagaacc ctcaggaagg cctgtacaat     180
gaactgcaga agataagat ggcggaggcc tacagtgaga ttgggatgaa aggcgagcgc      240
cggaggggca aggggcacga tggcctttac caggtctca gtacagccac caaggacacc     300
tacgacgccc ttcacatgca ggccctgccc cctcgc                               336

<210> SEQ ID NO 36
<211> LENGTH: 5934
<212> TYPE: DNA
<213> ORGANISM: Artificial sequence
<220> FEATURE:
<223> OTHER INFORMATION: PB vector

<400> SEQUENCE: 36
tgttgtttgc ccctcccccg tgccttcctt gaccctggaa ggtgccactc ccactgtcct      60
ttcctaataa aatgaggaaa ttgcatcgca ttgtctgagt aggtgtcatt ctattctggg     120
gggtggggtg gggcaggaca gcaagggga ggattgggaa gacaatagca ggcatgctgg     180
ggatgcggtg ggctctatgg cttctgaggc ggaaagaacc agctgggct cgactagagc      240 ttgcggaacc cttactcgag ataacttcgt ataatgtatg ctatacgaag ttatgctagc     300
caacaagctc gtcatcgctt tgcagaagag cagagaggat atgctcatcg tctaaagaac     360
tacccatttt attatatatt agtcacgata tctataacaa gaaaatatat atataataag     420
ttatcacgta agtagaacat gaaataacaa tataattatc gtatgagtta aatcttaaaa     480
gtcacgtaaa agataatcat gcgtcatttt gactcacgcg gtcgttatag ttcaaaatca     540
gtgacactta ccgcattgac aagcacgcct cacgggagct ccaagcggcg actgagatgt     600
cctaaatgca cagcgacgga ttcgcgctat ttagaaagag agagcaatat ttcaagaatg     660
catgcgtcaa ttttacgcag actatctttc tagggttaaa aaagatttgc gctttactcg     720
acctaaactt taaacacgtc atagaatctt cgtttgacaa aaaccacatt gtggccaagc     780
tgtgtgacgc gacgcgcgct aaagaatggc aaaccaagtc gcgcgaggta cccagctttt     840
gttcccttta gtgagggtta attccgagct tggcgtaatc atggtcatag ctgtttcctg     900
tgtgaaattg ttatccgctc acaattccac acaacatacg agccggaagc ataaagtgta     960
aagcctgggg tgcctaatga gtgagctaac tcacattaat tgcgttgcgc tcactgcccg    1020

```
ctttccagtc gggaaacctg tcgtgccagc tgcattaatg aatcggccaa cgcgcgggga    1080
gaggcggttt gcgtattggg cgctcttccg cttcctcgct cactgactcg ctgcgctcgg    1140
tcgttcggct gcggcgagcg gtatcagctc actcaaaggc ggtaatacgg ttatccacag    1200
aatcagggga taacgcagga aagaacatgt gagcaaaagg ccagcaaaag gccaggaacc    1260
gtaaaaaggc cgcgttgctg gcgtttttcc ataggctccg cccccctgac gagcatcaca    1320
aaaatcgacg ctcaagtcag aggtggcgaa acccgacagg actataaaga taccaggcgt    1380
ttccccctgg aagctccctc gtgcgctctc ctgttccgac cctgccgctt accggatacc    1440
tgtccgcctt tctcccttcg ggaagcgtgg cgctttctca tagctcacgc tgtaggtatc    1500
tcagttcggt gtaggtcgtt cgctccaagc tgggctgtgt gcacgaaccc cccgttcagc    1560
ccgaccgctg cgccttatcc ggtaactatc gtcttgagtc caacccggta agacacgact    1620
tatcgccact ggcagcagcc actggtaaca ggattagcag agcgaggtat gtaggcggtg    1680
ctacagagtt cttgaagtgg tggcctaact acggctacac tagaaggaca gtatttggta    1740
tctgcgctct gctgaagcca gttaccttcg gaaaaagagt tggtagctct tgatccggca    1800
aacaaaccac cgctggtagc ggtggttttt ttgtttgcaa gcagcagatt acgcgcagaa    1860
aaaaaggatc tcaagaagat cctttgatct tttctacggg gtctgacgct cagtggaacg    1920
aaaactcacg ttaagggatt ttggtcatga gattatcaaa aaggatcttc acctagatcc    1980 tttttaaatta aaaatgaagt tttaaatcaa tctaaagtat atatgagtaa acttggtctg    2040
acagttacca atgcttaatc agtgaggcac ctatctcagc gatctgtcta tttcgttcat    2100
ccatagttgc ctgactcccc gtcgtgtaga taactacgat acgggagggc ttaccatctg    2160
gccccagtgc tgcaatgata ccgcgagacc cacgctcacc ggctccagat ttatcagcaa    2220
taaaccagcc agccggaagg gccgagcgca gaagtggtcc tgcaacttta tccgcctcca    2280
tccagtctat taattgttgc cgggaagcta gagtaagtag ttcgccagtt aatagtttgc    2340
gcaacgttgt tgccattgct acaggcatcg tggtgtcacg ctcgtcgttt ggtatggctt    2400
cattcagctc cggttcccaa cgatcaaggc gagttacatg atcccccatg ttgtgcaaaa    2460
aagcggttag ctccttcggt cctccgatcg ttgtcagaag taagttggcc gcagtgttat    2520
cactcatggt tatggcagca ctgcataatt ctcttactgt catgccatcc gtaagatgct    2580
tttctgtgac tggtgagtac tcaaccaagt cattctgaga atagtgtatg cggcgaccga    2640
gttgctcttg cccggcgtca atacgggata ataccgcgcc acatagcaga actttaaaag    2700
tgctcatcat tggaaaacgt tcttcggggc gaaaactctc aaggatctta ccgctgttga    2760
gatccagttc gatgtaaccc actcgtgcac ccaactgatc ttcagcatct tttactttca    2820
ccagcgtttc tgggtgagca aaaacaggaa ggcaaaatgc cgcaaaaaag ggaataaggg    2880
cgacacggaa atgttgaata ctcatactct tcctttttca atattattga agcatttatc    2940
agggttattg tctcatgagc ggatacatat ttgaatgtat ttagaaaaat aaacaaatag    3000
gggttccgcg cacatttccc cgaaaagtgc cacctgggaa attgtaaacg ttaatatttt    3060
gttaaaattc gcgttaaatt tttgttaaat cagctcattt tttaaccaat aggccgaaat    3120
cggcaaaatc ccttataaat caaaagaata gaccgagata gggttgagtg ttgttccagt    3180
ttggaacaag agtccactat taaagaacgt ggactccaac gtcaaagggc gaaaaaccgt    3240
ctatcagggc gatggcccac tacgtgaacc atcaccctaa tcaagttttt tggggtcgag    3300
gtgccgtaaa gcactaaatc ggaaccctaa agggagcccc cgatttagag cttgacgggg    3360
```

-continued

```
aaagccggcg aacgtggcga gaaaggaagg gaagaaagcg aaaggagcgg gcgctagggc      3420
gctggcaagt gtagcggtca cgctgcgcgt aaccaccaca cccgccgcgc ttaatgcgcc      3480
gctacagggc gcgtcgcgcc attcgccatt caggctgcgc aactgttggg aagggcgatc      3540
ggtgcgggcc tcttcgctat tacgccagct ggcgaaaggg ggatgtgctg caaggcgatt      3600
aagttgggta acgccagggt tttcccagtc acgacgttgt aaaacgacgg ccagtgaatt      3660
gtaatacgac tcactatagg gcgaattgga gctcggtatt cacgacagca ggctgaataa      3720
taaaaaaatt agaaactatt atttaaccct agaaagataa tcatattgtg acgtacgtta      3780
aagataatca tgcgtaaaat tgacgcatgt gttttatcgg tctgtatatc gaggtttatt      3840
tattaatttg aatagatatt aagttttatt atatttacac ttacatacta ataataaatt      3900
caacaaacaa tttatttatg tttatttatt tattaaaaaa aaacaaaaac tcaaaatttc      3960
ttctataaag taacaaaact tttaaacatt ctctctttta caaaaataaa cttattttgt      4020
actttaaaaa cagtcatgtt gtattataaa ataagtaatt agcttaacct atacataata      4080
gaaacaaatt atacttatta gtcagtcaga aacaactttg gcacatatca atattatgct      4140
ctcgttaatc gcataacttc gtataatgta tgctatacga agttataatt cagatctttc      4200
ggcgcgccgg gtcgacattg attattgact agttattaat agtaatcaat tacggggtca      4260
ttagttcata gcccatatat ggagttccgc gttacataac ttacggtaaa tggcccgcct      4320
ggctgaccgc ccaacgaccc ccgcccattg acgtcaataa tgacgtatgt tcccatagta      4380
acgccaatag ggactttcca ttgacgtcaa tgggtggact atttacggta aactgcccac      4440
ttggcagtac atcaagtgta tcatatgcca agtacgcccc ctattgacgt caatgacggt      4500
aaatggcccg cctggcatta tgcccagtac atgaccttat gggactttcc tacttggcag      4560
tacatctacg tattagtcat cgctattacc atgggtcgag gtgagcccca cgttctgctt      4620
cactctcccc atctcccccc cctccccacc cccaattttg tatttattta ttttttaatt      4680
attttgtgca gcgatggggg cggggggggg ggggcgcgc gccaggcggg gcggggcggg      4740
gcgaggggcg gggcggggcg aggcggagag gtgcggcggc agccaatcag agcggcgcgc      4800
tccgaaagtt cctttttatg gcgaggcggc ggcggcggcg gccctataaa aagcgaagcg      4860
cgcggcgggc gggagtcgct gcgttgcctt cgccccgtgc cccgctccgc gccgcctcgc      4920
gccgcccgcc ccggctctga ctgaccgcgt tactcccaca ggtgagcggg cgggacggcc      4980
cttctcctcc gggctgtaat tagcgcttgg tttaatgacg gctcgtttct tttctgtggc      5040
tgcgtgaaag ccttaaaggg ctccgggagg gccctttgtg cggggggggag cggctcgggg      5100 ggtgcgtgcg tgtgtgtgtg cgtggggagc gccgcgtgcg gcccgcgctg cccggcggct      5160
gtgagcgctg cgggcgcggc gcggggcttt gtgcgctccg cgtgtgcgcg aggggagcgc      5220
ggccgggggc ggtgccccgc ggtgcggggg ggctgcgagg ggaacaaagg ctgcgtgcgg      5280
ggtgtgtgcg tgggggggtg agcaggggtg gtgggcgcgg cggtcgggct gtaacccccc      5340
cctgcacccc cctccccgag ttgctgagca cggcccggct tcgggtgcgg ggctccgtgc      5400
ggggcgtggc gcggggctcg ccgtgccggg cgggggtgg cggcaggtgg gggtgccggg      5460
cggggcgggg ccgcctcggg ccggggaggg ctcgggggag gggcgcggcg gccccggagc      5520
gccggcggct gtcgaggcgc ggcgagccgc agccattgcc ttttatggta atcgtgcgag      5580
agggcgcagg gacttccttt gtcccaaatc tggcggagcc gaaatctggg aggcgccgcc      5640 gcacccctc tagcgggcgc gggcgaagcg gtgcggcgcc ggcaggaagg aaatgggcgg      5700
ggagggcctt cgtgcgtcgc cgcgccgccg tccccttctc catctccagc ctcggggctg      5760
```

```
ccgcagggggg acggctgcct tcgggggggga cggggcaggg cggggttcgg cttctggcgt     5820
gtgaccggcg gctctagagc ctctgctaac catgttcatg ccttcttctt tttcctacag     5880
ctcctgggca acgtgctggt tgttgtgctg tctcatcatt ttggcaaaga attc           5934

<210> SEQ ID NO 37
<211> LENGTH: 30
<212> TYPE: DNA
<213> ORGANISM: Artificial sequence
<220> FEATURE:
<223> OTHER INFORMATION: NFAT

<400> SEQUENCE: 37
ggaggaaaaa ctgtttcata cagaaggcgt                                        30

<210> SEQ ID NO 38
<211> LENGTH: 105
<212> TYPE: DNA
<213> ORGANISM: Artificial sequence
<220> FEATURE:
<223> OTHER INFORMATION: IL2 promoter

<400> SEQUENCE: 38
agatctagac tctagagggt atataatgga agctcgaatt ccagcttggc attccggtac      60
tgttggtaaa aagcttggca atccggtact gttggtaaag ccacc                     105

<210> SEQ ID NO 39
<211> LENGTH: 81
<212> TYPE: DNA
<213> ORGANISM: Artificial sequence
<220> FEATURE:
<223> OTHER INFORMATION: 2A

<400> SEQUENCE: 39
aaaattgtcg ctcctgtcaa acaaactctt aactttgatt tactcaaact ggctggggat      60
gtagaaagca atccaggtcc a                                                 81

<210> SEQ ID NO 40
<211> LENGTH: 720
<212> TYPE: DNA
<213> ORGANISM: Artificial sequence
<220> FEATURE:
<223> OTHER INFORMATION: GFP

<400> SEQUENCE: 40
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgaccta cggcgtgcag tgcttcagcc gctaccccga ccacatgaag     240
cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacaa cagccacaac gtctatatca tggccgacaa gcagaagaac     480
ggcatcaagg tgaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
```
ctgctggagt tcgtgaccgc cgccgggatc actctcggca tggacgagct gtacaagtaa      720

<210> SEQ ID NO 41
<211> LENGTH: 4254
<212> TYPE: DNA
<213> ORGANISM: Artificial sequence
<220> FEATURE:
<223> OTHER INFORMATION: PB-TRE

<400> SEQUENCE: 41
gctcgctgat cagcctcgac tgtgccttct agttgccagc catctgttgt ttgcccctcc       60
cccgtgcctt ccttgaccct ggaaggtgcc actcccactg tcctttccta ataaaatgag      120
gaaattgcat cgcattgtct gagtaggtgt cattctattc tggggggtgg ggtggggcag      180
gacagcaagg gggaggattg ggaagacaat agcaggcatg ctggggatgc ggtgggctct      240
atggcttctg aggcggaaag aaccagctgg ggctcgacta gagcttgcgg aacccttact      300
cgagataact tcgtataatg tatgctatac gaagttatgc tagccaacaa gctcgtcatc      360
gctttgcaga agagcagaga ggatatgctc atcgtctaaa gaactaccca ttttattata      420
tattagtcac gatatctata acaagaaaat atatatataa taagttatca cgtaagtaga      480
acatgaaata acaatataat tatcgtatga gttaaatctt aaaagtcacg taaaagataa      540
tcatgcgtca ttttgactca cgcggtcgtt atagttcaaa atcagtgaca cttaccgcat      600
tgacaagcac gcctcacggg agctccaagc ggcgactgag atgtcctaaa tgcacagcga      660
cggattcgcg ctatttagaa agagagagca atatttcaag aatgcatgcg tcaattttac      720
gcagactatc tttctagggt taaaaaagat ttgcgcttta ctcgacctaa actttaaaca      780
cgtcatagaa tcttcgtttg acaaaaacca cattgtggcc aagctgtgtg acgcgacgcg      840
cgctaaagaa tggcaaacca agtcgcgcga ggtacccagc ttttgttccc tttagtgagg      900
gttaattccg agcttggcgt aatcatggtc atagctgttt cctgtgtgaa attgttatcc      960
gctcacaatt ccacacaaca tacgagccgg aagcataaag tgtaaagcct ggggtgccta     1020
atgagtgagc taactcacat taattgcgtt gcgctcactg cccgctttcc agtcgggaaa     1080
cctgtcgtgc cagctgcatt aatgaatcgg ccaacgcgcg gggagaggcg gtttgcgtat     1140
tgggcgctct tccgcttcct cgctcactga ctcgctgcgc tcggtcgttc ggctgcggcg     1200
agcggtatca gctcactcaa aggcggtaat acggttatcc acagaatcag gggataacgc     1260
aggaaagaac atgtgagcaa aaggccagca aaaggccagg aaccgtaaaa aggccgcgtt     1320
gctggcgttt ttccataggc tccgcccccc tgacgagcat cacaaaaatc gacgctcaag     1380
tcagaggtgg cgaaacccga caggactata aagataccag gcgtttcccc ctggaagctc     1440
cctcgtgcgc tctcctgttc cgaccctgcc gcttaccgga tacctgtccg cctttctccc     1500
ttcgggaagc gtggcgcttt ctcatagctc acgctgtagg tatctcagtt cggtgtaggt     1560
cgttcgctcc aagctgggct gtgtgcacga accccccgtt cagcccgacc gctgcgcctt     1620
atccggtaac tatcgtcttg agtccaaccc ggtaagacac gacttatcgc cactggcagc     1680
agccactggt aacaggatta gcagagcgag gtatgtaggc ggtgctacag agttcttgaa     1740
gtggtggcct aactacggct acactagaag gacagtattt ggtatctgcg ctctgctgaa     1800
gccagttacc ttcggaaaaa gagttggtag ctcttgatcc ggcaaacaaa ccaccgctgg     1860
tagcggtggt ttttttgttt gcaagcagca gattacgcgc agaaaaaaag gatctcaaga     1920
agatcctttg atcttttcta cggggtctga cgctcagtgg aacgaaaact cacgttaagg     1980
gattttggtc atgagattat caaaaaggat cttcacctag atccttttaa attaaaaatg     2040

```
aagtttttaaa tcaatctaaa gtatatatga gtaaacttgg tctgacagtt accaatgctt    2100
aatcagtgag gcacctatct cagcgatctg tctatttcgt tcatccatag ttgcctgact    2160
ccccgtcgtg tagataacta cgatacggga gggcttacca tctggcccca gtgctgcaat    2220
gataccgcga gacccacgct caccggctcc agatttatca gcaataaacc agccagccgg    2280
aagggccgag cgcagaagtg gtcctgcaac tttatccgcc tccatccagt ctattaattg    2340
ttgccgggaa gctagagtaa gtagttcgcc agttaatagt ttgcgcaacg ttgttgccat    2400
tgctacaggc atcgtggtgt cacgctcgtc gtttggtatg gcttcattca gctccggttc    2460
ccaacgatca aggcgagtta catgatcccc catgttgtgc aaaaaagcgg ttagctcctt    2520
cggtcctccg atcgttgtca gaagtaagtt ggccgcagtg ttatcactca tggttatggc    2580
agcactgcat aattctctta ctgtcatgcc atccgtaaga tgcttttctg tgactggtga    2640
gtactcaacc aagtcattct gagaatagtg tatgcggcga ccgagttgct cttgcccggc    2700
gtcaatacgg gataataccg cgccacatag cagaacttta aaagtgctca tcattggaaa    2760
acgttcttcg gggcgaaaac tctcaaggat cttaccgctg ttgagatcca gttcgatgta    2820
acccactcgt gcacccaact gatcttcagc atcttttact ttcaccagcg tttctgggtg    2880
agcaaaaaca ggaaggcaaa atgccgcaaa aaagggaata agggcgacac ggaaatgttg    2940
aatactcata ctcttccttt ttcaatatta ttgaagcatt tatcagggtt attgtctcat    3000
gagcggatac atatttgaat gtatttagaa aaataaacaa ataggggttc cgcgcacatt    3060
tccccgaaaa gtgccacctg ggaaattgta aacgttaata tttttgttaaa attcgcgtta    3120 aatttttgtt aaatcagctc attttttaac caataggccg aaatcggcaa aatcccttat    3180
aaatcaaaag aatagaccga gatagggttg agtgttgttc cagtttggaa caagagtcca    3240
ctattaaaga acgtggactc caacgtcaaa gggcgaaaaa ccgtctatca gggcgatggc    3300
ccactacgtg aaccatcacc ctaatcaagt tttttggggt cgaggtgccg taaagcacta    3360
aatcggaacc ctaaagggag cccccgattt agagcttgac ggggaaagcc ggcgaacgtg    3420
gcgagaaagg aagggaagaa agcgaaagga gcgggcgcta gggcgctggc aagtgtagcg    3480
gtcacgctgc gcgtaaccac cacacccgcc gcgcttaatg cgccgctaca gggcgcgtcg    3540
cgccattcgc cattcaggct gcgcaactgt tgggaagggc gatcggtgcg ggcctcttcg    3600
ctattacgcc agctggcgaa aggggggatgt gctgcaaggc gattaagttg ggtaacgcca    3660
gggttttccc agtcacgacg ttgtaaaacg acggccagtg aattgtaata cgactcacta    3720
tagggcgaat tggagctcgg tattcacgac agcaggctga ataataaaaa aattagaaac    3780
tattatttaa ccctagaaag ataatcatat tgtgacgtac gttaaagata atcatgcgta    3840
aaattgacgc atgtgtttta tcggtctgta tatcgaggtt tatttattaa tttgaataga    3900
tattaagttt tattatattt acacttacat actaataata aattcaacaa acaatttatt    3960
tatgtttatt tatttattaa aaaaaaacaa aaactcaaaa tttcttctat aaagtaacaa    4020
aacttttaaa cattctctct tttacaaaaa taaacttatt ttgtacttta aaaacagtca    4080
tgttgtatta taaaataagt aattagctta acctatacat aatagaaaca aattatactt    4140
attagtcagt cagaaacaac tttggcacat atcaatatta tgctctcgtt aatcgcataa    4200
cttcgtataa tgtatgctat acgaagttat aattcagatc tttcggcgcg ccgg          4254
```

<210> SEQ ID NO 42
<211> LENGTH: 2497
<212> TYPE: DNA

<213> ORGANISM: Artificial sequence
<220> FEATURE:
<223> OTHER INFORMATION: PB-CAG-rtTA

<400> SEQUENCE: 42

```
agctttgcaa agatggataa agttttaaac agagaggaat ctttgcagct aatggacctt      60
ctaggtcttg aaaggagtgg gaattggctc cggtgcccgt cagtgggcag agcgcacatc     120
gcccacagtc cccgagaagt tggggggagg ggtcggcaat tgaaccggtg cctagagaag     180
gtggcgcggg gtaaactggg aaagtgatgt cgtgtactgg ctccgccttt ttcccgaggg     240
tgggggagaa ccgtatataa gtgcagtagt cgccgtgaac gttctttttc gcaacgggtt     300
tgccgccaga acacaggtaa gtgccgtgtg tggttcccgc gggcctggcc tctttacggg     360
ttatggccct tgcgtgcctt gaattacttc cactggctgc agtacgtgat tcttgatccc     420
gagcttcggg ttggaagtgg gtgggagagt tcgaggcctt gcgcttaagg agccccttcg     480
cctcgtgctt gagttgaggc ctggcctggg cgctggggcc gccgcgtgcg aatctggtgg     540
caccttcgcg cctgtctcgc tgctttcgat aagtctctag ccatttaaaa ttttgatga     600 cctgctgcga cgctttttt ctggcaagat agtcttgtaa atgcgggcca agatctgcac     660
actggtattt cggtttttgg ggccgcgggc ggcgacgggg cccgtgcgtc ccagcgcaca     720
tgttcggcga ggcggggcct gcgagcgcgg ccaccgagaa tcggacgggg gtagtctcaa     780
gctggccggc ctgctctggt gcctggcctc gcgccgccgt gtatcgcccc gccctgggcg     840
gcaaggctgg cccggtcggc accagttgcg tgagcggaaa gatggccgct tcccggccct     900
gctgcaggga gctcaaaatg gaggacgcgg cgctcgggag agcgggcggg tgagtcaccc     960
acacaaagga aaagggcctt tccgtcctca gccgtcgctt catgtgactc cacggagtac    1020
cgggcgccgt ccaggcacct cgattagttc tcgagctttt ggagtacgtc gtctttaggt    1080
tggggggagg ggttttatgc gatggagttt ccccacactg agtgggtgga gactgaagtt    1140
aggccagctt ggcacttgat gtaattctcc ttggaatttg ccctttttga gtttggatct    1200
tggttcattc tcaagcctca gacagtggtt caaagttttt ttcttccatt tcaggtgtcg    1260
tgaggaattt cgacatttaa atttaattaa tctcgacggt atcggttaac ttttaaaaga    1320
aaagggggga ttgggggta cagtgcaggg gaaagaatag tagacataat agcaacagac    1380
atacaaacta aagaattaca aaaacaaatt acaaaaattc aaaattttcc gatcacgaga    1440
ctagcctcga ggtttaaact acgggatccg gccattacgg ccgaattcca ccatgtctag    1500
attagataaa agtaaagtga ttaacagcgc attagagctg cttaatgagg tcggaatcga    1560
aggtttaaca acccgtaaac tcgcccagaa gcttggtgta gagcagccta cactgtattg    1620
gcatgtaaaa aataagcggg ctttgctcga cgccttagcc attgagatgt tagataggca    1680
ccatactcac ttttgcccct taaaaggga aagctggcaa gatttttac gcaataacgc    1740 taaaagtttt agatgtgctt tactaagtca tcgcaatgga gcaaaagtac attcagatac    1800
acggcctaca gaaaaacagt atgaaactct cgaaaatcaa ttagcctttt tatgccaaca    1860
aggtttttca ctagagaacg cgttatatgc actcagcgct gtggggcatt ttactttagg    1920
ttgcgtattg gaagatcaag agcatcaagt cgctaaagaa gaaagggaaa cacctactac    1980
tgatagtatg ccgccattat tacgacaagc tatcgaatta tttgatcacc aaggtgcaga    2040
gccagccttc ttattcggcc ttgaattgat catatgcgga ttagaaaaac aacttaaatg    2100
tgaaagtggg tccgcgtaca gccgcgcgcg tacgaaaaac aattacgggt ctaccatcga    2160
gggcctgctc gatctcccgg acgacgacgc ccccgaagag gcggggctgg cggctccgcg    2220
```

-continued

```
cctgtccttt ctccccgcgg gacacacgcg cagactgtcg acggcccccc cgaccgatgt    2280
cagcctgggg gacgagctcc acttagacgg cgaggacgtg gcgatggcgc atgccgacgc    2340
gctagacgat ttcgatctgg acatgttggg ggacgggat tccccgggtc cgggatttac      2400
cccccacgac tccgcccct acggcgctct ggatatggcc gacttcgagt ttgagcagat      2460
gtttaccgat gcccttggaa ttgacgagta cggtggg                              2497
```

<210> SEQ ID NO 43
<211> LENGTH: 2053
<212> TYPE: DNA
<213> ORGANISM: Artificial sequence
<220> FEATURE:
<223> OTHER INFORMATION: PB-PL623

<400> SEQUENCE: 43

```
agagacggcc gcatcttctt gtgcagtgcc agcctcgtcc cgtagacaaa cctgcaggat      60
gggcagcagc ctggacgacg agcacatcct gagcgccctg ctgcagagcg acgacgagct     120
ggtcggcgag gacagcgaca gcgaggtgag cgaccacgtg agcgaggacg acgtgcagtc     180
cgacaccgag gaggccttca tcgacgaggt gcacgaggtg cagcctacca gcagcggctc     240
cgagatcctg gacgagcaga acgtgatcga gcagcccggc agctccctgg ccagcaacag     300
gatcctgacc ctgccccaga ggaccatcag gggcaagaac aagcactgct ggtccacctc     360
caagcccacc aggcggagca gggtgtccgc cctgaacatc gtgagaagcc agaggggccc     420
caccaggatg tgcaggaaca tctacgaccc cctgctgtgc ttcaagctgt tcttcaccga     480
cgagatcatc agcgagatcg tgaagtggac caacgccgag atcagcctga gaggcggga     540 gagcatgacc tccgccacct tcagggacac caacgaggac gagatctacg ccttcttcgg     600
catcctggtg atgaccgccg tgaggaagga caaccacatg agcaccgacg acctgttcga     660
cagatccctg agcatggtgt acgtgagcgt gatgagcagg gacagattcg acttcctgat     720
cagatgcctg aggatggacg acaagagcat caggcccacc ctgcgggaga cgacgtgtt     780 cacccccgtg agaaagatct gggacctgtt catccaccag tgcatccaga actacacccc     840
tggcgcccac ctgaccatcg acgagcagct gctgggcttc aggggcaggt gcccccttcag    900 ggtctatatc cccaacaagc ccagcaagta cggcatcaag atcctgatga tgtgcgacag     960
cggcaccaag tacatgatca acggcatgcc ctacctgggc aggggcaccc agaccaacgg    1020
cgtgcccctg ggcgagtact acgtgaagga gctgtccaag cccgtccacg gcagctgcag    1080
aaacatcacc tgcgacaact ggttcaccag catcccccctg gccaagaacc tgctgcagga    1140
gccctacaag ctgaccatcg tgggcaccgt gagaagcaac aagagagaga tccccgaggt    1200
cctgaagaac agcaggtcca ggcccgtggg caccagcatg ttctgcttcg acggcccccct    1260 gaccctggtg tcctacaagc ccaagcccgc caagatggtg tacctgctgt ccagctgcga    1320
cgaggacgcc agcatcaacg agagcaccgg caagcccccag atggtgatgt actacaacca    1380
gaccaagggc ggcgtggaca ccctggacca gatgtgcagc gtgatgacct gcagcagaaa    1440
gaccaacagg tggcccatgg ccctgctgta cggcatgatc aacatcgcct gcatcaacag    1500
cttcatcatc tacagccaca acgtgagcag caagggcgaa aaggtgcaga gccggaaaaa    1560
gttcatgcgg aacctgtaca tgggcctgac ctccagcttc atgaggaaga ggctggaggc    1620
ccccaccctg aagagatacc tgaggggacaa catcagcaac atcctgccca aagaggtgcc    1680
cggcaccagc gacgacagca ccgaggagcc cgtgatgaag aagaggacct actgcaccta    1740
```

```
ctgtcccagc aagatcagaa gaaaggccag cgccagctgc aagaagtgta agaaggtcat   1800
ctgccgggag cacaacatcg acatgtgcca gagctgtttc tgattaatta agaaaccctg   1860
gaccacccac cccagcaagg acactgagca agagaggccc tatcccaact cggcccccaa   1920
cactgagcat ctccctcaca atttccatcc cagaccccca taataacagg aggggcctag   1980
ggagccctcc ctactctctt gaataccatc aataaagttc gctgcaccca caaaaaaaaa   2040
aaaaaaaaaa aaa                                                       2053

<210> SEQ ID NO 44
<211> LENGTH: 9601
<212> TYPE: DNA
<213> ORGANISM: Artificial sequence
<220> FEATURE:
<223> OTHER INFORMATION: pWPXLd

<400> SEQUENCE: 44
gataatcaac ctctggatta caaaatttgt gaaagattga ctggtattct taactatgtt     60 gctccttta cgctatgtgg atacgctgct ttaatgcctt tgtatcatgc tattgcttcc    120
cgtatggctt tcattttctc ctccttgtat aaatcctggt tgctgtctct ttatgaggag    180
ttgtggcccg ttgtcaggca acgtggcgtg gtgtgcactg tgtttgctga cgcaacccccc   240 actggttggg gcattgccac cacctgtcag ctcctttccg ggactttcgc tttcccccctc   300 cctattgcca cggcggaact catcgccgcc tgccttgccc gctgctggac aggggctcgg    360
ctgttgggca ctgacaattc cgtggtgttg tcggggaagc tgacgtcctt ccatggctg    420 ctcgcctgtg ttgccacctg gattctgcgc gggacgtcct tctgctacgt cccttcggcc    480
ctcaatccag cggaccttcc ttcccgcggc ctgctgccgg ctctgcggcc tcttccgcgt    540
cttcgccttc gccctcagac gagtcggatc tccctttggg ccgcctcccc gcatcggtac    600
gtatggccag gtacctttaa gaccaatgac ttacaaggca gctgtagatc ttagccactt    660
tttaaaagaa aaggggggac tggaagggct aattcactcc caacgaagac aagatctgct    720
ttttgcttgt actgggtctc tctggttaga ccagatctga gcctgggagc tctctggcta    780
actagggaac ccactgctta agcctcaata aagcttgcct tgagtgcttc aagtagtgtg    840
tgcccgtctg ttgtgtgact ctggtaacta gagatccctc agacccttt agtcagtgtg    900 gaaaatctct agcagcatct agaattaatt ccgtgtattc tatagtgtca cctaaatcgt    960
atgtgtatga tacataaggt tatgtattaa ttgtagccgc gttctaacga caatatgtac   1020
aagcctaatt gtgtagcatc tggcttactg aagcagaccc tatcatctct ctcgtaaact   1080
gccgtcagag tcggtttggt tggacgaacc ttctgagttt ctggtaacgc cgtcccgcac   1140
ccggaaatgg tcagcgaacc aatcagcagg gtcatcgcta gccagatcct ctacgccgga   1200
cgcatcgtgg ccggcatcac cggcgccaca ggtgcggttg ctggcgccta tatcgccgac   1260
atcaccgatg gggaagatcg ggctcgccac ttcgggctca tgagcgcttg tttcggcgtg   1320
ggtatggtgg caggccccgt ggccggggga ctgttgggcg ccatctcctt gcatgcacca   1380
ttccttgcgg cggcggtgct caacggcctc aacctactac tgggctgctt cctaatgcag   1440
gagtcgcata agggagagcg tcgaatggtg cactctcagt acaatctgct ctgatgccgc   1500
atagttaagc cagccccgac acccgccaac acccgctgac gcgccctgac gggcttgtct   1560
gctcccggca tccgcttaca gacaagctgt gaccgtctcc gggagctgca tgtgtcagag   1620
gttttcaccg tcatcaccga aacgcgcgag acgaaagggc ctcgtgatac gcctattttt   1680
ataggttaat gtcatgataa taatggtttc ttagacgtca ggtggcactt ttcggggaaa   1740
```

-continued

```
tgtgcgcgga acccctattt gtttattttt ctaaatacat tcaaatatgt atccgctcat    1800
gagacaataa ccctgataaa tgcttcaata atattgaaaa aggaagagta tgagtattca    1860
acatttccgt gtcgccctta ttcccttttt tgcggcattt tgccttcctg tttttgctca    1920
cccagaaacg ctggtgaaag taaaagatgc tgaagatcag ttgggtgcac gagtgggtta    1980
catcgaactg gatctcaaca gcggtaagat ccttgagagt tttcgccccg aagaacgttt    2040
tccaatgatg agcactttta aagttctgct atgtggcgcg gtattatccc gtattgacgc    2100
cgggcaagag caactcggtc gccgcataca ctattctcag aatgacttgg ttgagtactc    2160
accagtcaca gaaaagcatc ttacggatgg catgacagta agagaattat gcagtgctgc    2220
cataaccatg agtgataaca ctgcggccaa cttacttctg acaacgatcg gaggaccgaa    2280
ggagctaacc gctttttttgc acaacatggg ggatcatgta actcgccttg atcgttggga    2340
accggagctg aatgaagcca taccaaacga cgagcgtgac accacgatgc ctgtagcaat    2400
ggcaacaacg ttgcgcaaac tattaactgg cgaactactt actctagctt cccggcaaca    2460
attaatagac tggatggagg cggataaagt tgcaggacca cttctgcgct cggcccttcc    2520
ggctggctgg tttattgctg ataaatctgg agccggtgag cgtgggtctc gcggtatcat    2580
tgcagcactg gggccagatg gtaagccctc ccgtatcgta gttatctaca cgacggggag    2640
tcaggcaact atggatgaac gaaatagaca gatcgctgag ataggtgcct cactgattaa    2700
gcattggtaa ctgtcagacc aagtttactc atatatactt tagattgatt taaaacttca    2760
tttttaattt aaaaggatct aggtgaagat cctttttgat aatctcatga ccaaaatccc    2820
ttaacgtgag ttttcgttcc actgagcgtc agaccccgta gaaaagatca aggatcttc    2880 ttgagatcct ttttttctgc gcgtaatctg ctgcttgcaa acaaaaaaac caccgctacc    2940
agcggtggtt tgtttgccgg atcaagagct accaactctt tttccgaagg taactggctt    3000
cagcagagcg cagataccaa atactgtcct tctagtgtag ccgtagttag gccaccactt    3060
caagaactct gtagcaccgc ctacatacct cgctctgcta tcctgttac cagtggctgc    3120 tgccagtggc gataagtcgt gtcttaccgg gttggactca agacgatagt taccggataa    3180
ggcgcagcgg tcgggctgaa cggggggttc gtgcacacag cccagcttgg agcgaacgac    3240
ctacaccgaa ctgagatacc tacagcgtga gcattgagaa agcgccacgc ttcccgaagg    3300
gagaaaggcg gacaggtatc cggtaagcgg cagggtcgga acaggagagc gcacgaggga    3360
gcttccaggg ggaaacgcct ggtatcttta tagtcctgtc gggtttcgcc acctctgact    3420
tgagcgtcga tttttgtgat gctcgtcagg ggggcggagc ctatggaaaa acgccagcaa    3480
cgcggccttt ttacggttcc tggccttttg ctggcctttt gctcacatgt tctttcctgc    3540
gttatcccct gattctgtgg ataaccgtat taccgccttt gagtgagctg ataccgctcg    3600
ccgcagccga acgaccgagc gcagcgagtc agtgagcgag gaagcggaag agcgcccaat    3660
acgcaaaccg cctctccccg cgcgttggcc gattcattaa tgcagctgtg gaatgtgtgt    3720
cagttagggt gtggaaagtc cccaggctcc ccagcaggca gaagtatgca aagcatgcat    3780
ctcaattagt cagcaaccag gtgtggaaag tccccaggct ccccagcagg cagaagtatg    3840
caaagcatgc atctcaatta gtcagcaacc atagtcccgc ccctaactcc gcccatcccg    3900
cccctaactc cgcccagttc cgcccattct ccgccccatg gctgactaat tttttttatt    3960
tatgcagagg ccgaggccgc ctcggcctct gagctattcc agaagtagtg aggaggcttt    4020
tttggaggcc taggcttttg caaaaagctt ggacacaaga caggcttgcg agatatgttt    4080
```

```
gagaatacca ctttatcccg cgtcagggag aggcagtgcg taaaaagacg cggactcatg   4140
tgaaatactg gttttttagtg cgccagatct ctataatctc gcgcaaccta ttttcccctc   4200
gaacactttt taagccgtag ataaacaggc tgggacactt cacatgagcg aaaaatacat   4260
cgtcacctgg gacatgttgc agatccatgc acgtaaactc gcaagccgac tgatgccttc   4320
tgaacaatgg aaaggcatta ttgccgtaag ccgtggcggt ctgtaccggg tgcgttactg   4380
gcgcgtgaac tgggtattcg tcatgtcgat accgtttgta tttccagcta cgatcacgac   4440
aaccagcgcg agcttaaagt gctgaaacgc gcagaaggcg atggcgaagg cttcatcgtt   4500
attgatgacc tggtggatac cggtggtact gcggttgcga ttcgtgaaat gtatccaaaa   4560
gcgcactttg tcaccatctt cgcaaaaccg gctggtcgtc cgctggttga tgactatgtt   4620
gttgatatcc cgcaagatac ctggattgaa cagccgtggg atatgggcgt cgtattcgtc   4680
ccgccaatct ccggtcgcta atctttttcaa cgcctggcac tgccgggcgt tgttctttttt  4740 aacttcaggc gggttacaat agtttccagt aagtattctg gaggctgcat ccatgacaca   4800
ggcaaacctg agcgaaaccc tgttcaaacc ccgctttaaa catcctgaaa cctcgacgct   4860
agtccgccgc tttaatcacg gcgcacaacc gcctgtgcag tcggcccttg atggtaaaac   4920
catccctcac tggtatcgca tgattaaccg tctgatgtgg atctggcgcg gcattgaccc   4980
acgcgaaatc ctcgacgtcc aggcacgtat tgtgatgagc gatgccgaac gtaccgacga   5040
tgatttatac gatacggtga ttggctaccg tggcggcaac tggatttatg agtgggcccc   5100
ggatctttgt gaaggaacct tacttctgtg gtgtgacata attggacaaa ctacctacag   5160
agatttaaag ctctaaggta aatataaaat ttttaagtgt ataatgtgtt aaactactga   5220
ttctaattgt ttgtgtattt tagattccaa cctatggaac tgatgaatgg gagcagtggt   5280
ggaatgcctt taatgaggaa aacctgtttt gctcagaaga aatgccatct agtgatgatg   5340
aggctactgc tgactctcaa cattctactc ctccaaaaaa gaagagaaag gtagaagacc   5400
ccaaggactt tccttcagaa ttgctaagtt ttttgagtca tgctgtgttt agtaatagaa   5460
ctcttgcttg ctttgctatt tacaccacaa aggaaaaagc tgcactgcta tacaagaaaa   5520
ttatggaaaa atattctgta acctttataa gtaggcataa cagttataat cataacatac   5580
tgttttttct tactccacac aggcatagag tgtctgctat taataactat gctcaaaaat   5640
tgtgtacctt tagcttttta atttgtaaag gggttaataa ggaatatttg atgtatagtg   5700
ccttgactag agatcataat cagccatacc acatttgtag aggttttact tgctttaaaa   5760
aacctcccac acctccccct gaacctgaaa cataaaatga atgcaattgt tgttgttaac   5820
ttgtttattg cagcttataa tggttacaaa taaagcaata gcatcacaaa tttcacaaat   5880
aaagcatttt tttcactgca ttctagttgt ggtttgtcca aactcatcaa tgtatcttat   5940
catgtctgga tcaactggat aactcaagct aaccaaaatc atcccaaact tcccacccca   6000
taccctatta ccactgccaa ttacctagtg gtttcattta ctctaaacct gtgattcctc   6060
tgaattattt tcattttaaa gaaattgtat ttgttaaata tgtactacaa acttagtagt   6120
tggaagggct aattcactcc caaagaagac aagatatcct tgatctgtgg atctaccaca   6180
cacaaggcta cttccctgat tagcagaact acacaccagg gccagggggtc agatatccac   6240 tgacctttgg atggtgctac aagctagtac cagttgagcc agataaggta gaagaggcca   6300
ataaaggaga gaacaccagc ttgttacacc ctgtgagcct gcatgggatg gatgacccgg   6360
agagagaagt gttagagtgg aggtttgaca gccgcctagc atttcatcac gtggcccgag   6420
agctgcatcc ggagtacttc aagaactgct gatatcgagc ttgctacaag ggactttccg   6480
```

-continued

```
ctggggactt tccagggagg cgtggcctgg gcgggactgg ggagtggcga gccctcagat   6540
cctgcatata agcagctgct ttttgcctgt actgggtctc tctggttaga ccagatctga   6600
gcctgggagc tctctggcta actagggaac ccactgctta agcctcaata aagcttgcct   6660
tgagtgcttc aagtagtgtg tgcccgtctg ttgtgtgact ctggtaacta gagatccctc   6720
agaccctttt agtcagtgtg gaaaatctct agcagtggcg cccgaacagg gacttgaaag   6780
cgaaagggaa accagaggag ctctctcgac gcaggactcg gcttgctgaa gcgcgcacgg   6840
caagaggcga ggggcggcga ctggtgagta cgccaaaaat tttgactagc ggaggctaga   6900
aggagagaga tgggtgcgag agcgtcagta ttaagcgggg gagaattaga tcgcgatggg   6960
aaaaaattcg gttaaggcca gggggaaaga aaaaatataa attaaaacat atagtatggg   7020
caagcaggga gctagaacga ttcgcagtta atcctggcct gttagaaaca tcagaaggct   7080
gtagacaaat actgggacag ctacaaccat cccttcagac aggatcagaa gaacttagat   7140
cattatataa tacagtagca accctctatt gtgtgcatca aaggatagag ataaaagaca   7200
ccaaggaagc tttagacaag atagaggaag agcaaaacaa aagtaagacc accgcacagc   7260
aagcggccgc tgatcttcag acctggagga ggagatatga gggacaattg gagaagtgaa   7320
ttatataaat ataaagtagt aaaaattgaa ccattaggag tagcacccac caaggcaaag   7380
agaagagtgg tgcagagaga aaaaagagca gtgggaatag gagctttgtt ccttgggttc   7440
ttgggagcag caggaagcac tatgggcgca gcgtcaatga cgctgacggt acaggccaga   7500
caattattgt ctggtatagt gcagcagcag aacaatttgc tgagggctat tgaggcgcaa   7560
cagcatctgt tgcaactcac agtctggggc atcaagcagc tccaggcaag aatcctggct   7620
gtggaaagat acctaaagga tcaacagctc ctggggattt ggggttgctc tggaaaactc   7680
atttgcacca ctgctgtgcc ttggaatgct agttggagta taaatctct ggaacagatt   7740 tggaatcaca cgacctggat ggagtgggac agagaaatta caattacac aagcttaata   7800 cactccttaa ttgaagaatc gcaaaaccag caagaaaaga atgaacaaga attattggaa   7860
ttagataaat gggcaagttt gtggaattgg tttaacataa caaattggct gtggtatata   7920
aaattattca taatgatagt aggaggcttg gtaggtttaa gaatagtttt tgctgtactt   7980
tctatagtga atagagttag gcagggatat tcaccattat cgtttcagac ccacctccca   8040
accccgaggg gacccgacag gcccgaagga atagaagaag aaggtggaga gagacagaga   8100 cagatccaa ttcgattagt gaacggatct cgacggtatc gatgtcgacg ataagctttg   8160
caaagatgga taaagtttta aacagagagg aatctttgca gctaatggac cttctaggtc   8220
ttgaaaggag tgggaattgg ctccggtgcc cgtcagtggg cagagcgcac atcgcccaca   8280
gtccccgaga agttgggggg aggggtcggc aattgaaccg gtgcctagag aaggtggcgc   8340
ggggtaaact gggaaagtga tgtcgtgtac tggctccgcc ttttttcccga gggtggggga   8400 gaaccgtata taagtgcagt agtcgccgtg aacgttcttt ttcgcaacgg gtttgccgcc   8460
agaacacagg taagtgccgt gtgtggttcc cgcgggcctg gcctctttac gggttatggc   8520
ccttgcgtgc cttgaattac ttccactggc tgcagtacgt gattcttgat cccgagcttc   8580
gggttggaag tgggtgggag agttcgaggc cttgcgctta aggagcccct tcgcctcgtg   8640
cttgagttga ggcctggcct gggcgctggg gccgccgcgt gcgaatctgg tggcaccttc   8700
gcgcctgtct cgctgctttc gataagtctc tagccattta aaatttttga tgacctgctg   8760
cgacgctttt tttctggcaa gatagtcttg taaatgcggg ccaagatctg cacactggta   8820
```

-continued

```
tttcggtttt tggggccgcg ggcggcgacg gggcccgtgc gtcccagcgc acatgttcgg       8880
cgaggcgggg cctgcgagcg cggccaccga gaatcggacg ggggtagtct caagctggcc       8940
ggcctgctct ggtgcctggc ctcgcgccgc cgtgtatcgc cccgccctgg gcggcaaggc       9000
tggcccggtc ggcaccagtt gcgtgagcgg aaagatggcc gcttcccggc cctgctgcag       9060
ggagctcaaa atggaggacg cggcgctcgg gagagcgggc gggtgagtca cccacacaaa       9120
ggaaaagggc ctttccgtcc tcagccgtcg cttcatgtga ctccacggag taccgggcgc       9180
cgtccaggca cctcgattag ttctcgagct tttggagtac gtcgtcttta ggttgggggg       9240
aggggtttta tgcgatggag tttccccaca ctgagtgggt ggagactgaa gttaggccag       9300
cttggcactt gatgtaattc tccttggaat ttgccctttt tgagtttgga tcttggttca       9360
ttctcaagcc tcagacagtg gttcaaagtt tttttcttcc atttcaggtg tcgtgaggaa       9420
tttcgacatt taaatttaat taatctcgac ggtatcggtt aacttttaaa agaaaagggg       9480
ggattggggg gtacagtgca ggggaaagaa tagtagacat aatagcaaca gacatacaaa       9540
ctaaagaatt acaaaaacaa attacaaaaa ttcaaaattt tccgatcacg agactagcct       9600
c                                                                         9601

<210> SEQ ID NO 45
<211> LENGTH: 3591
<212> TYPE: DNA
<213> ORGANISM: Artificial sequence
<220> FEATURE:
<223> OTHER INFORMATION: PB vector

<400> SEQUENCE: 45
gatatctata acaagaaaat atatatataa taagttatca cgtaagtaga acatgaaata         60
acaatataat tatcgtatga gttaaatctt aaaagtcacg taaaagataa tcatgcgtca        120
ttttgactca cgcggtcgtt atagttcaaa atcagtgaca cttaccgcat tgacaagcac        180
gcctcacggg agctccaagc ggcgactgag atgtcctaaa tgcacagcga cggattcgcg        240
ctatttagaa agagagagca atatttcaag aatgcatgcg tcaattttac gcagactatc        300
tttctagggt taaaaaagat ttgcgcttta ctcgacctaa actttaaaca cgtcatagaa        360
tcttcgtttg acaaaaacca cattgtggcc aagctgtgtg acgcgacgcg cgctaaagaa        420
tggcaaacca agtcgcgcga ggtacccagc ttttgttccc tttagtgagg gttaattccg        480
agcttggcgt aatcatggtc atagctgttt cctgtgtgaa attgttatcc gctcacaatt        540
ccacacaaca tacgagccgg aagcataaag tgtaaagcct ggggtgccta atgagtgagc        600
taactcacat taattgcgtt gcgctcactg cccgctttcc agtcgggaaa cctgtcgtgc        660
cagctgcatt aatgaatcgg ccaacgcgcg gggagaggcg gtttgcgtat tgggcgctct        720
tccgcttcct cgctcactga ctcgctgcgc tcggtcgttc ggctgcggcg agcggtatca        780
gctcactcaa aggcggtaat acggttatcc acagaatcag gggataacgc aggaaagaac        840
atgtgagcaa aaggccagca aaaggccagg aaccgtaaaa aggccgcgtt gctggcgttt        900
ttccataggc tccgcccccc tgacgagcat cacaaaaatc gacgctcaag tcagaggtgg        960
cgaaacccga caggactata aagataccag gcgtttcccc ctggaagctc cctcgtgcgc       1020
tctcctgttc cgaccctgcc gcttaccgga tacctgtccg cctttctccc ttcgggaagc       1080
gtggcgcttt ctcatagctc acgctgtagg tatctcagtt cggtgtaggt cgttcgctcc       1140
aagctgggct gtgtgcacga accccccgtt cagcccgacc gctgcgcctt atccggtaac       1200
tatcgtcttg agtccaaccc ggtaagacac gacttatcgc cactggcagc agccactggt       1260
```

```
aacaggatta gcagagcgag gtatgtaggc ggtgctacag agttcttgaa gtggtggcct    1320
aactacggct acactagaag gacagtattt ggtatctgcg ctctgctgaa gccagttacc    1380
ttcggaaaaa gagttggtag ctcttgatcc ggcaaacaaa ccaccgctgg tagcggtggt    1440 tttttttgttt gcaagcagca gattacgcgc agaaaaaaag gatctcaaga agatcctttg    1500
atcttttcta cggggtctga cgctcagtgg aacgaaaact cacgttaagg gattttggtc    1560
atgagattat caaaaaggat cttcacctag atccttttaa attaaaaatg aagttttaaa    1620
tcaatctaaa gtatatatga gtaaacttgg tctgacagtt accaatgctt aatcagtgag    1680
gcacctatct cagcgatctg tctatttcgt tcatccatag ttgcctgact ccccgtcgtg    1740
tagataacta cgatacggga gggcttacca tctggcccca gtgctgcaat gataccgcga    1800
gacccacgct caccggctcc agatttatca gcaataaacc agccagccgg aagggccgag    1860
cgcagaagtg gtcctgcaac tttatccgcc tccatccagt ctattaattg ttgccgggaa    1920
gctagagtaa gtagttcgcc agttaatagt ttgcgcaacg ttgttgccat tgctacaggc    1980
atcgtggtgt cacgctcgtc gtttggtatg gcttcattca gctccggttc ccaacgatca    2040
aggcgagtta catgatcccc catgttgtgc aaaaaagcgg ttagctcctt cggtcctccg    2100
atcgttgtca gaagtaagtt ggccgcagtg ttatcactca tggttatggc agcactgcat    2160
aattctctta ctgtcatgcc atccgtaaga tgctttttctg tgactggtga gtactcaacc    2220
aagtcattct gagaatagtg tatgcggcga ccgagttgct cttgcccggc gtcaatacgg    2280
gataataccg cgccacatag cagaacttta aaagtgctca tcattggaaa acgttcttcg    2340
gggcgaaaac tctcaaggat cttaccgctg ttgagatcca gttcgatgta acccactcgt    2400
gcacccaact gatcttcagc atcttttact ttcaccagcg tttctgggtg agcaaaaaca    2460
ggaaggcaaa atgccgcaaa aaagggaata agggcgacac ggaaatgttg aatactcata    2520
ctcttccttt ttcaatatta ttgaagcatt tatcagggtt attgtctcat gagcggatac    2580
atatttgaat gtatttagaa aaataaacaa ataggggttc cgcgcacatt tccccgaaaa    2640
gtgccacctg ggaaattgta aacgttaata ttttgttaaa attcgcgtta aattttttgtt    2700 aaatcagctc attttttaac caataggccg aaatcggcaa aatcccttat aaatcaaaag    2760
aatagaccga gatagggttg agtgttgttc cagtttggaa caagagtcca ctattaaaga    2820
acgtggactc caacgtcaaa gggcgaaaaa ccgtctatca gggcgatggc ccactacgtg    2880
aaccatcacc ctaatcaagt tttttggggt cgaggtgccg taaagcacta atcggaacc    2940 ctaaagggag cccccgattt agagcttgac ggggaaagcc ggcgaacgtg gcgagaaagg    3000
aagggaagaa agcgaaagga gcgggcgcta gggcgctggc aagtgtagcg gtcacgctgc    3060
gcgtaaccac cacacccgcc gcgcttaatg cgccgctaca gggcgcgtcg cgccattcgc    3120
cattcaggct gcgcaactgt tgggaagggc gatcggtgcg ggcctcttcg ctattacgcc    3180
agctggcgaa aggggggatgt gctgcaaggc gattaagttg ggtaacgcca gggttttccc    3240
agtcacgacg ttgtaaaacg acggccagtg aattgtaata cgactcacta tagggcgaat    3300
tggagctcgg tattcacgac agcaggctga ataataaaaa aattagaaac tattatttaa    3360
ccctagaaag ataatcatat tgtgacgtac gttaaagata atcatgcgta aaattgacgc    3420
atgtgtttta tcggtctgta tatcgaggtt tatttattaa tttgaataga tattaagttt    3480
tattatattt acacttacat actaataata aattcaacaa acaatttatt tatgtttatt    3540
tatttattaa aaaaaaacaa aaactcaaaa tttcttctat aaagtaacaa a            3591
```